US007385681B2

(12) United States Patent
Ninomiya et al.

(10) Patent No.: US 7,385,681 B2
(45) Date of Patent: Jun. 10, 2008

(54) GAS LEAKAGE MONITORING METHOD AND ITS SYSTEM

(75) Inventors: Hideki Ninomiya, Takamatsu (JP); Koji Ichikawa, Takamatsu (JP); Ken Kawahara, Takamatsu (JP); Hirofumi Miki, Takamatsu (JP); Tasuku Moriya, Takamatsu (JP)

(73) Assignee: Shikoku Research Institute Incorporated, Takamatsu-shi, Kagawa (JP)

( * ) Notice: Subject to any disclaimer, the term of this patent is extended or adjusted under 35 U.S.C. 154(b) by 95 days.

(21) Appl. No.: 10/548,194

(22) PCT Filed: Mar. 5, 2004

(86) PCT No.: PCT/JP2004/002868

§ 371 (c)(1),
(2), (4) Date: Sep. 7, 2005

(87) PCT Pub. No.: WO2004/079350

PCT Pub. Date: Sep. 16, 2004

(65) Prior Publication Data

US 2006/0238741 A1      Oct. 26, 2006

(30) Foreign Application Priority Data

Mar. 7, 2003   (JP)   ............... 2003-060820
Aug. 8, 2003   (JP)   ............... 2003-290329
Oct. 28, 2003  (JP)   ............... 2003-367905

(51) Int. Cl.
*G01C 3/08* (2006.01)
(52) U.S. Cl. .................................... 356/5.01
(58) Field of Classification Search ................ 356/5.01
See application file for complete search history.

(56) References Cited

U.S. PATENT DOCUMENTS

| 3,723,007 | A | 3/1973 | Leonard |
| 2002/0118352 | A1 | 8/2002 | Ohzu et al. |
| 2004/0051867 | A1* | 3/2004 | Brestel et al. ............... 356/318 |

FOREIGN PATENT DOCUMENTS

GB         1337357        11/1973

(Continued)

*Primary Examiner*—Thomas H. Tarcza
*Assistant Examiner*—Luke Ratcliffe
(74) *Attorney, Agent, or Firm*—Westerman, Hattori, Daniels & Adrian, LLP.

(57) ABSTRACT

A gas leakage monitoring method and system capable of ensuring safety of a gas utilization facility by visualizing invisible-to-naked-eye leakage gas and/or flame of leakage gas into the form of an image. The gas leakage monitoring method comprises the steps of collecting a detected light of a particular wavelength, which is caused by leakage gas and/or a flame of the leakage gas, in a space to be monitored, converting the detected light into an electronic image, amplifying and then converting the electronic image into an optical image again, and imaging the spatial intensity distribution of the particular wavelength light. The gas leakage monitoring system comprises first means for collecting a detected light of a particular wavelength, which is caused by leakage gas and/or a flame of the leakage gas, in a space to be monitored, second means for converting the detected light into an electronic image, and amplifying and then converting the electronic image into an optical image again, and third means for imaging the spatial intensity distribution of the particular wavelength light.

18 Claims, 28 Drawing Sheets

FOREIGN PATENT DOCUMENTS

| | | | |
|---|---:|---|---:|
| IL | 151745 | * | 9/2002 |
| JP | 49-100997 | | 9/1974 |
| JP | 4-48398 | | 2/1992 |
| JP | 4-205299 | | 7/1992 |
| JP | 6-288858 | | 10/1994 |
| JP | 9-178566 | | 7/1997 |
| JP | 11-142238 | | 5/1999 |
| JP | 2001-23055 | | 1/2001 |
| JP | 2002250769 | | 9/2002 |

* cited by examiner

H₂:0%

H₂:4%

H₂:10%

H₂:50%

H₂:50%

H₂:100%

GAS LEAKAGE MONITORING METHOD AND ITS SYSTEM

TECHNICAL FIELD

The present invention relates to a technique for visualizing invisible-to-naked-eye gas and/or flame into the form of an image, thereby, for example, remotely determining the presence or absence of a gas leakage and/or a flame, a leakage point, and a high-temperature dangerous region with high safety. More particularly, the present invention relates to a gas leakage monitoring method and system, which are adapted for continuous monitoring and are suitably used for, e.g., the operation of a hydrogen gas utilization facility, such as hydrogen supply stations and fuel cells, and monitoring of a hydrogen gas leakage.

BACKGROUND ART

Hitherto, leakage gas has been detected by bringing sucked gas into direct contact with a sensor portion and measuring gas concentration based on a change in value of electrical resistance or current. However, such a known gas detector is of the sensor type that an area capable of being monitored by one detector is narrow and leakage gas cannot be detected unless the gas reaches the detector. Accordingly, there has been a risk that, in the event of a gas leakage, an alarm error may occur depending on the direction of wind and the position where the detector is installed. Another problem is that, in a gas refinery or the like, a very large number of gas detectors must be installed and a substantial cost is required (see Patent Reference 1).

On the other hand, to solve the above-mentioned problem, a gas visualizing device for remotely monitoring the presence of a gas leakage has been proposed. Such a gas visualizing device employs a laser beam source for irradiating an infrared laser beam having the same wavelength as the absorption wavelength of gas to be measured, and the absorption of an infrared ray, which is reflected from the background, is imaged using an image sensor to be displayed in the form of a two-dimensional visible image.

However, that known gas visualizing device requires a very large-sized and high-power laser beam source and therefore has a serious problem in point of cost. Another problem is that the displayed two-dimensional image is greatly affected by weather conditions and temperatures, and a difficulty arises in discriminating the occurrence of a gas leakage from shinning of sunlight. For those reasons, the known gas visualizing device has not been suitable for monitoring a gas leakage in practical fields (see Patent Reference 2).

Further, in the case of hydrogen gas, in spite of being an energy medium with a high risk in such a point as causing explosion if ignited, the hydrogen gas is tasteless, colorless, and odorless. In addition, even if ignited, a flame of hydrogen gas is substantially transparent and invisible to the naked eye under sunlight. Meanwhile, several publications disclose detection techniques of selecting ultraviolet light generated upon the occurrence of corona discharge by an interference filter, collecting an ultraviolet ray having passed through the interference filter, and visualizing the collected ultraviolet ray in the form of a visible image using an ultraviolet image tube or a TV camera (see Patent References 3 and 4).

| | |
|---|---|
| Patent Reference 1 | Japanese Patent Laid-open No. 6-307967 |
| Patent Reference 2 | Japanese Patent Laid-open No. 6-288858 |
| Patent Reference 3 | Japanese Patent Publication No. 5-40874 |
| Patent Reference 4 | Japanese Utility Model Laid-open No. 61-174680 |

DISCLOSURE OF THE INVENTION

In environments utilizing and storing gases, it has been usual that a gas leakage is monitored by installing a stationary gas detector in a place where the gas tends to reside, while locating the leakage point has been performed by personnel carrying a portable gas detector and going round of inspection. In particular, hydrogen gas is very difficult to locate the leakage point for the reasons that the hydrogen gas is tasteless, colorless, and odorless and the known city gas detector or the like cannot be used, as it is, to detect the hydrogen gas because of different properties of those gases. Accordingly, there has been demanded a monitoring technique capable of detecting a gas leakage and locating the leakage point in a continuous manner.

Also, a device for detecting ultraviolet rays generated from flames and issuing an alarm has been put into practical use. However, when a flame is invisible to the naked eye under sunlight in the daytime (e.g., in the case of a hydrogen flame), it has been difficult to take an optimum action because of incapability in safely locating the ignition point even with such a device being operated. In addition, that device covers a wide range of wavelength of ultraviolet rays as a detection target and therefore may detect even an ultraviolet ray (e.g., sunlight reflected by a window glass) other than those generated from flames in some cases. This leads to a problem that the device is susceptible to malfunction and reliability is insufficient.

Further, because a region where hot air generated by a flame is ejected and reside, or actual temperatures around wall surfaces, pipes, etc., which are heated to high temperatures, cannot be sensed with the naked eye, a difficulty arises in confirming a high-temperature region around the flame, thus making it harder to stop the leakage gas and perform extinguishing activities.

When observing a flame by a thermo-camera for visualizing an infrared ray, radiation from high-temperature portions, such as wall surfaces and pipes heated by the flame, is so strong that it is difficult to locate the flame shape and the position where the flame is generated.

In addition, a device for detecting an infrared ray generated from a flame and issuing an alarm has been further put into practice, but such a device has also not yet succeeded in overcoming the difficulty in confirming a high-temperature region around the flame.

An object of the present invention is to solve the problems set forth above.

More specifically, an object of the present invention is to provide a gas leakage monitoring method and system, which can realize the following demands:

1. Visualization of leakage gas
2. Visualization of a flame
3. Visualization of a high-temperature dangerous region With the view of realizing those demands, the present invention is intended, on the basis of the Raman scattering phenomenon that when a laser beam is irradiated to gas or a liquid, the wavelength of the laser beam is shifted by an amount of energy corresponding to the absorption energy of a molecule, to detect a gas leakage by imaging the spatial intensity distribution of the Raman scattering light and to locate a leakage point by superimposing a distribution image over a background image.

Also, the present invention is intended, upon the occurrence of a flame, to detect an ultraviolet ray generated from the flame, to detect the occurrence of the flame by amplifying and imaging a weak light of a particular wavelength, and to locate a frame generation point and/or a high-temperature dangerous region by superimposing a background image and/or a flame image and/or an infrared ray image with each other.

According to one aspect of the present invention, there is provided a gas leakage monitoring method comprising the steps of collecting, in a target space to be monitored, a detection target light of a particular wavelength generated from leakage gas and/or a flame of the leakage gas, converting the collected light into an electronic image, amplifying the electronic image, and converting the amplified electronic image into an optical image again, thereby imaging a spatial intensity distribution of the particular wavelength light.

According to another aspect of the present invention, the detection target light generated from the leakage gas is a Raman scattering light generated from measurement target gas with irradiation of a laser beam to the target space to be monitored.

According to still another aspect of the present, the detection target light of the particular wavelength is collected by an optical band-pass filter having a transmission wavelength center in match with the wavelength of a spectrum line of the Raman scattering light generated from the measurement target gas.

According to still another aspect of the present invention, the detection target light of the particular wavelength is collected only for a certain time calculated based on a return time of the laser beam or the Raman scattering light.

According to still another aspect of the present invention, a gas leakage point is located by superimposing a background image of the target space to be monitored and the imaged spatial intensity distribution of the Raman scattering light with each other.

According to still another aspect of the present invention, a distance to the gas leakage point is calculated based on a return time of the laser beam or the Raman scattering light.

According to still another aspect of the present invention, the detection target light generated from a fire of the leakage gas is an ultraviolet light.

According to still another aspect of the present invention the detection target light of the particular wavelength is collected by an optical band-pass filter having a transmission wavelength center in match with the wavelength of an emission spectrum line of an OH-group.

According to still another aspect of the present invention, the gas leakage monitoring method further comprises the steps of collecting an infrared light of a particular wavelength in the target space to be monitored, converting the collected light into an electronic image, amplifying the electronic image, and converting the amplified electronic image into an optical image again, thereby imaging a spatial intensity distribution of the infrared light in the target space to be monitored; and superimposing the imaged spatial intensity distribution of the infrared light and the imaged spatial intensity distribution of the particular wavelength light with each other, thereby locating a flame generation point of the leakage gas.

According to still another aspect of the present invention, the gas leakage monitoring method further comprises the steps of collecting an infrared light of a particular wavelength in the target space to be monitored, converting the collected light into an electronic image, amplifying the electronic image, and converting the amplified electronic image into an optical image again, thereby imaging a spatial intensity distribution of the infrared light in the target space to be monitored; and superimposing the imaged spatial intensity distribution of the infrared light and the background image of the target space to be monitored with each other, thereby locating a high-temperature dangerous region.

According to still another aspect of the present invention, in the step of collecting the infrared light of the particular wavelength in the target space to be monitored, a transmission light is selected by an optical band-pass filter allowing an infrared spectrum of 7 µm to 14 µm to pass through the filter.

According to still another aspect of the present invention, there is provided a gas leakage monitoring system comprising first means for collecting, in a target space to be monitored, a detection target light of a particular wavelength generated from leakage gas and/or a flame of the leakage gas; second means for converting the collected detection target light into an electronic image, amplifying the electronic image, and converting the amplified electronic image into an optical image again; and third means for imaging a spatial intensity distribution of the particular wavelength light.

According to still another aspect of the present invention, the gas leakage monitoring system further comprises means for irradiating a laser beam to the target space to be monitored, wherein the first means comprises a condenser lens and an optical band-pass filter having a transmission wavelength center in match with the wavelength of a spectrum line of the Raman scattering light generated from the measurement target gas; the second means comprises an image intensifier, an image pickup device, and a signal processing unit; and the third means is a program for imaging a detected signal.

According to still another aspect of the present invention, the gas leakage monitoring system further comprises synchronizing signal transmission means for synchronizing the laser beam irradiation means and the second means with each other, the synchronizing signal transmission means operating the second means only for a certain time calculated based on a return time of the laser beam or the Raman scattering light.

According to still another aspect of the present invention, the first means and the laser beam irradiation means are disposed in coaxial relation.

According to still another aspect of the present invention, the gas leakage monitoring system further comprises means for picking up a background image of the target space to be monitored; and means for superimposing the spatial intensity distribution of the particular wavelength light imaged by the third means and the background image picked up by the background image pickup means with each other, thereby locating a gas leakage point.

According to still another aspect of the present invention, the gas leakage monitoring system further comprises means for calculating a distance to the gas leakage point based on a return time of the laser beam or the Raman scattering light.

According to still another aspect of the present invention, the first means comprises a condenser lens and an optical band-pass filter having a transmission wavelength center in match with the wavelength of an emission spectrum line of an OH-group; the second means comprises an image intensifier, an image pickup device, and a signal processing unit; and the third means is a program for imaging a detected signal.

According to still another aspect of the present invention, the first means comprises a condenser lens, a first optical band-pass filter having a transmission wavelength center in match with the wavelength of a spectrum line of the Raman scattering light generated from the measurement target gas, and a second optical band-pass filter having a transmission wavelength center in match with the wavelength of an emission spectrum line of an OH-group; the second means comprises an image intensifier, an image pickup device, and a signal processing unit; and the third means is a program for imaging a detected signal, the first means being capable of using the first optical band-pass filter and the second optical band-pass filter in a switchable manner.

According to still another aspect of the present invention, the gas leakage monitoring system further comprises means for picking up a background image of the target space to be monitored; and means for superimposing the spatial intensity distribution of the particular wavelength light imaged by the third means and the background image picked up by the background image pickup means with each other, thereby locating a flame generation point of the leakage gas.

According to still another aspect of the present invention, the gas leakage monitoring system further comprises infrared image pickup means for collecting an infrared light of a particular wavelength in the target space to be monitored, converting the collected light into an electronic image, amplifying the electronic image, and converting the amplified electronic image into an optical image again; and means for superimposing the background image picked up by the background image pickup means and the infrared image picked up by the infrared image pickup means, thereby locating a high-temperature dangerous region.

According to still another aspect of the present invention, the infrared image pickup means comprises a condenser lens, an optical band-pass filter allowing an infrared spectrum of 7 μm to 14 μm to pass through the filter, and a thermo-camera.

Figure 1:
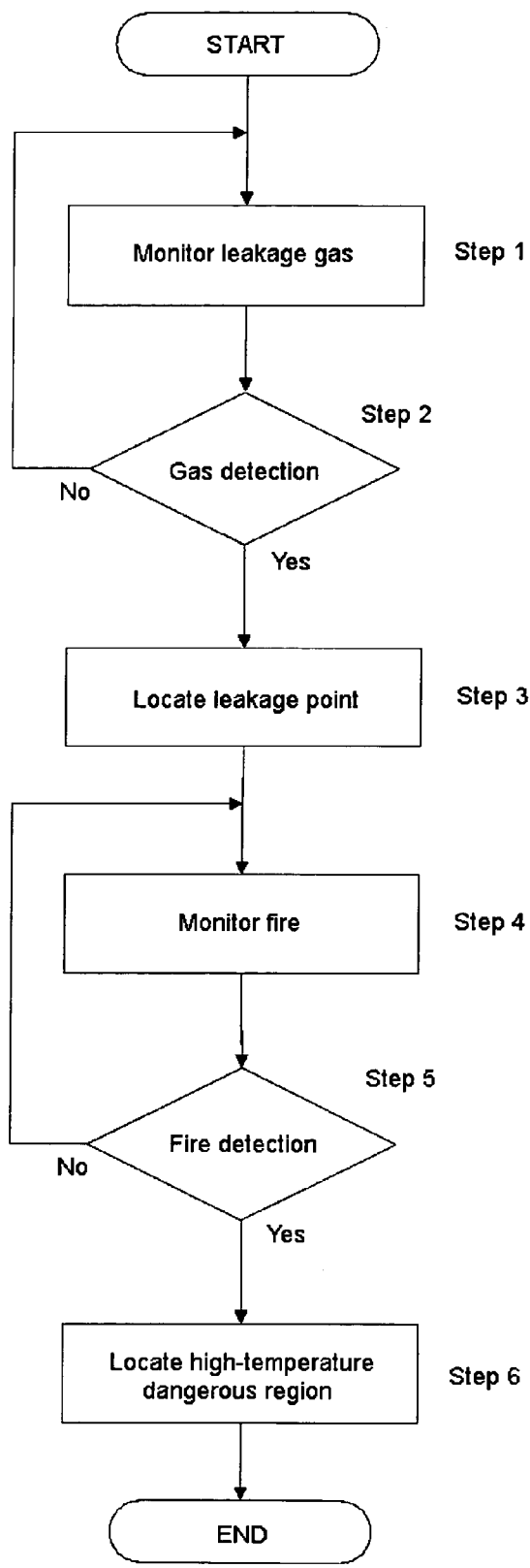
FIG. 1 is a flowchart of a gas leakage monitoring method according to the present invention.

REFERENCE NUMERALS 1 light receiving optical system, 2 objective lens, 3 optical band-path filter, 4 image intensifier, 5 eyepiece, 6 photoelectric surface, 7 electronic lens, 8 micro-channel plate, 9 fluorescent surface, 10 personal computer (PC), 11 CCD camera adapted for Raman scattering light, 12 CCD camera adapted for visible light, 13 monitoring control program, 14 image processing program, 15, 16, 17 image memory, 18 monitor screen, 19 speaker (alarm device), 20 LAN (communication means), 21 display of gas generation position, 30 thermo-camera, 40 condenser lens, 41 laser beam scanner, 42 oscillating mirror, 43, 44 photo detector, 45 laser unit, 46 beam distributor, 47 control/processing unit, 200 laser beam transmission system, 201 laser unit, 202 transmission optical system, and 203 time synchronizing signal generator

BEST MODE FOR CARRYING OUT THE INVENTION

The best mode for carrying out the present invention will be described below with reference to the drawings.

FIG. 1 is a flowchart showing an outline of processing executed in a gas leakage monitoring method and system according to the present invention. Steps 1 to 3 represent a process for visualizing leakage gas, and steps 4 to 6 represent a process for visualizing a flame. As shown in FIG. 1, monitoring of leakage gas is continued until gas detection (steps 1 and 2). If leakage gas is detected, a leakage point is located (step 3). After the gas detection, monitoring of a flame is continued until flame detection (steps 4 and 5). If a flame is detected, a high-temperature dangerous region is located (step 6).

While FIG. 1 is illustrated as monitoring a flame after the detection of leakage gas, the steps 1 to 3 and the steps 4 to 6 may be performed separately not in a time sequential order.

Procedures of the leakage gas visualizing process executed in the steps 1 to 3 will be described in more detail below.

Figure 2:
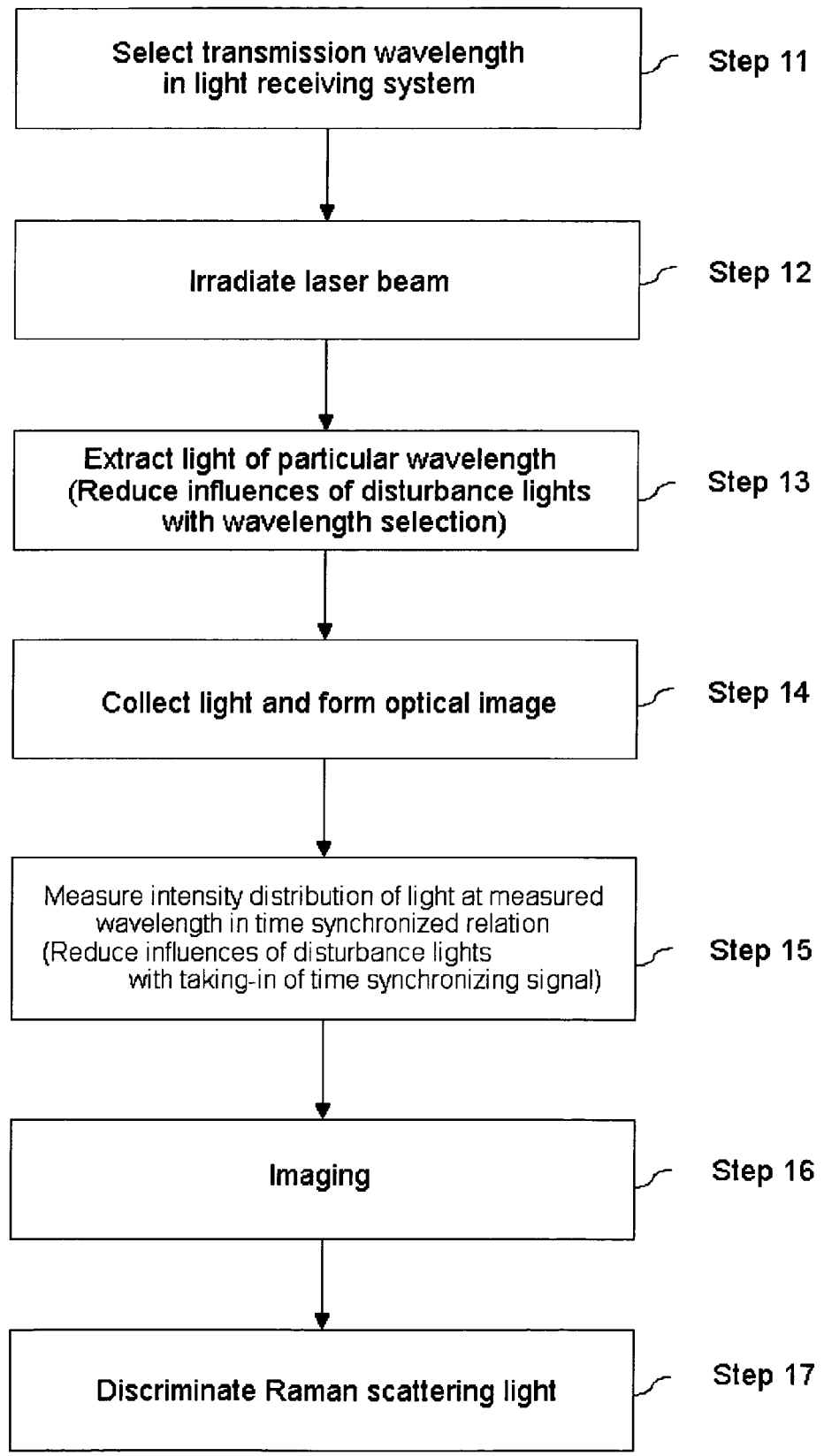
FIG. 2 is a flowchart showing an outline of a leakage gas detecting process according to the present invention.

The process for detecting leakage gas is performed as shown in FIG. 2. First, an optical band-path filter is selected to set a wavelength for observing a Raman scattering light (step 11). Because the Raman scattering wavelength differs for each type of gas to be monitored as listed in Table 1 given below, it is required to prepare a plurality of optical band-path filters having different centers of transmission wavelengths and select suitable one from among them. Then, a pulsing laser beam is irradiated to a space to be monitored (step 12), and a light of only a particular wavelength is extracted from Raman scattering lights induced from the leakage gas upon irradiation of the laser beam (step 13). The extracted light is collected and converted into an electronic image, followed by amplifying the electronic image and converting it into an optical image again, whereby the optical image is formed (step 14). On that occasion, noises due to disturbance lights, etc. can be cut by synchronizing the timing of collecting the Raman scattering light with the timing of irradiating the laser beam pulse to the monitored space (step 15). Then, the intensity of the Raman scattering light is converted into an electrical signal by an image pickup device, and the spatial intensity distribution of the Raman scattering light is obtained in the form of a visible image based on the recorded signal (step 16). The necessity of taking any action for the leakage gas, such as issuance of an alarm, is determined depending on whether the spatial intensity distribution of the Raman scattering light exceeds a threshold (step 17).

When sunlight or an object having a high photo-reflectance for other illumination light comes into the view field of an image pickup means, the signal intensity is increased in both the wavelength range of the Raman scattering light and the other wavelength range. In such a case, the real Raman scattering light cannot be regarded as being detected and therefore the detection of a gas leakage is not determined.

Figure 3:
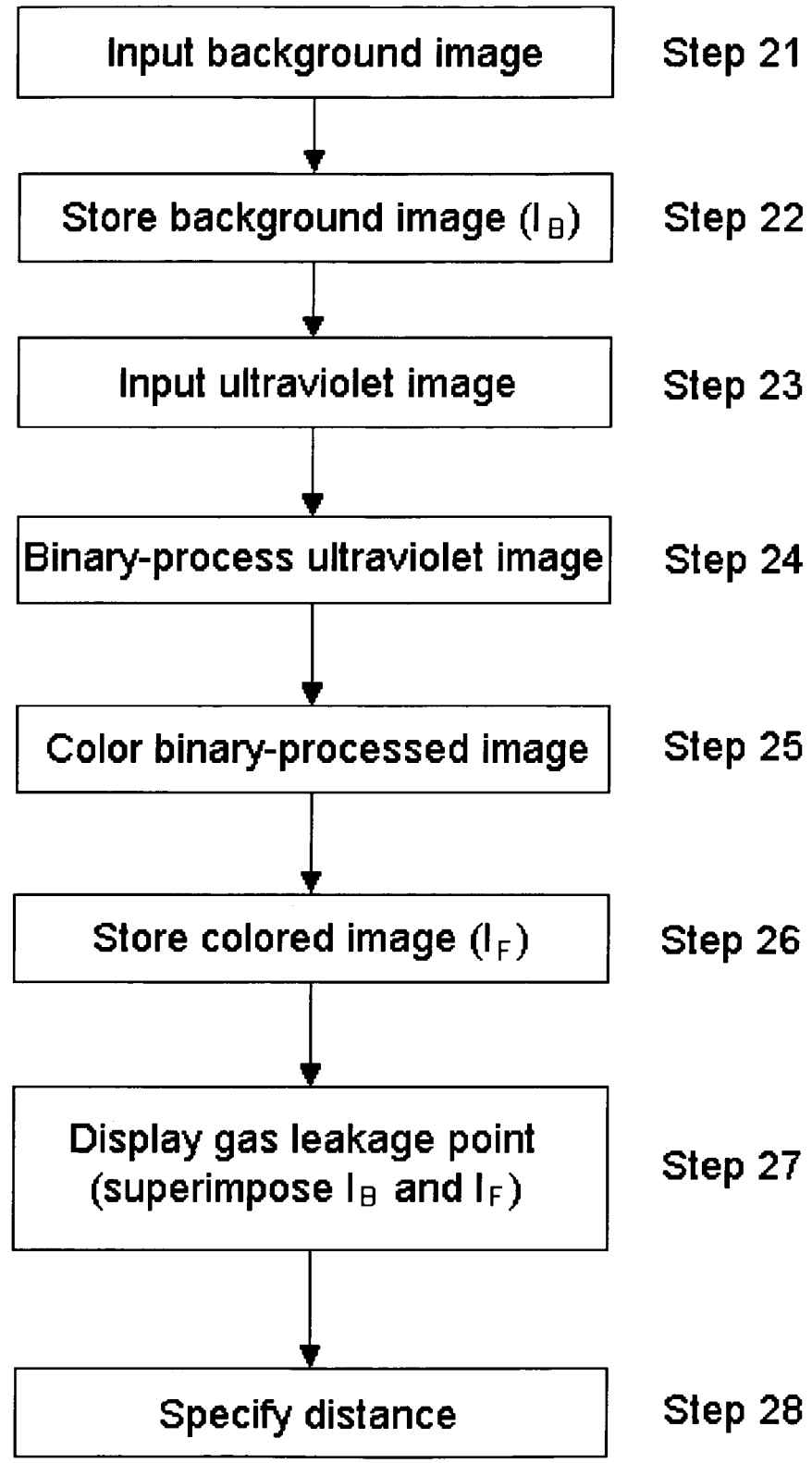
FIG. 3 is a flowchart of a process for locating a gas leakage point according to the present invention.

The process for locating a gas leakage point is performed as shown in FIG. 3. A background image (visible image) $I_B$ of the monitored space is picked up by a background image pickup means such as a CCD camera (step 21), and the background image $I_B$ is stored in an image processing system (step 22). Then, the ultraviolet image having been imaged in the step 16 is captured into the image processing system (step 23), and is subjected to binary processing to leave only areas of the ultraviolet image having values of not less than a threshold (step 24). A resulting binary-processed image is colored (step 25), and a colored image $I_F$ is stored in the image processing system (step 26). By superimposing the background image $I_B$ and the colored image $I_F$ with each other, the gas leakage point is visualized so that the gas leakage point can be located (step 27). The distance to the gas leakage point can be calculated from a return time of the laser scattering light or the Raman scattering light, or it can also be calculated based on triangular surveying when there are a plurality of image pickup means (step 28).

TABLE 1

| Molecule | Raman shift ($cm^{-1}$) | Raman scattering wavelength (nm) for laser wavelength of 355 nm | Raman scattering wavelength (nm) for laser wavelength of 266 nm | Raman scattering cross-sectional area for $N_2$ |
|---|---|---|---|---|
| $CO_2$ | 1286 | 372.0 | 275.4 | 1.1 |
| $CO_2$ | 1388 | 373.4 | 276.2 | 1.5 |
| $O_2$ | 1556 | 375.8 | 277.5 | 1.3 |
| CO | 2145 | 384.3 | 282.1 | 1.0 |
| $N_2$ | 2331 | 387.0 | 283.6 | 1.0 |
| $H_2S$ | 2611 | 391.3 | 285.9 | 6.8 |
| $CH_4$ | 2914 | 396.0 | 288.4 | 11.5 |
| $CH_4$ | 3020 | 397.6 | 289.2 | 5.0 |
| $NH_3$ | 3334 | 402.7 | 291.9 | 5.4 |
| $H_2O$ | 3652 | 407.9 | 294.6 | 2.8 |
| $H_2$ | 4160 | 416.5 | 299.1 | 3.1 |

Procedures of the flame visualizing process executed in the steps 4 to 6 will be described in more detail below.

Figure 4:
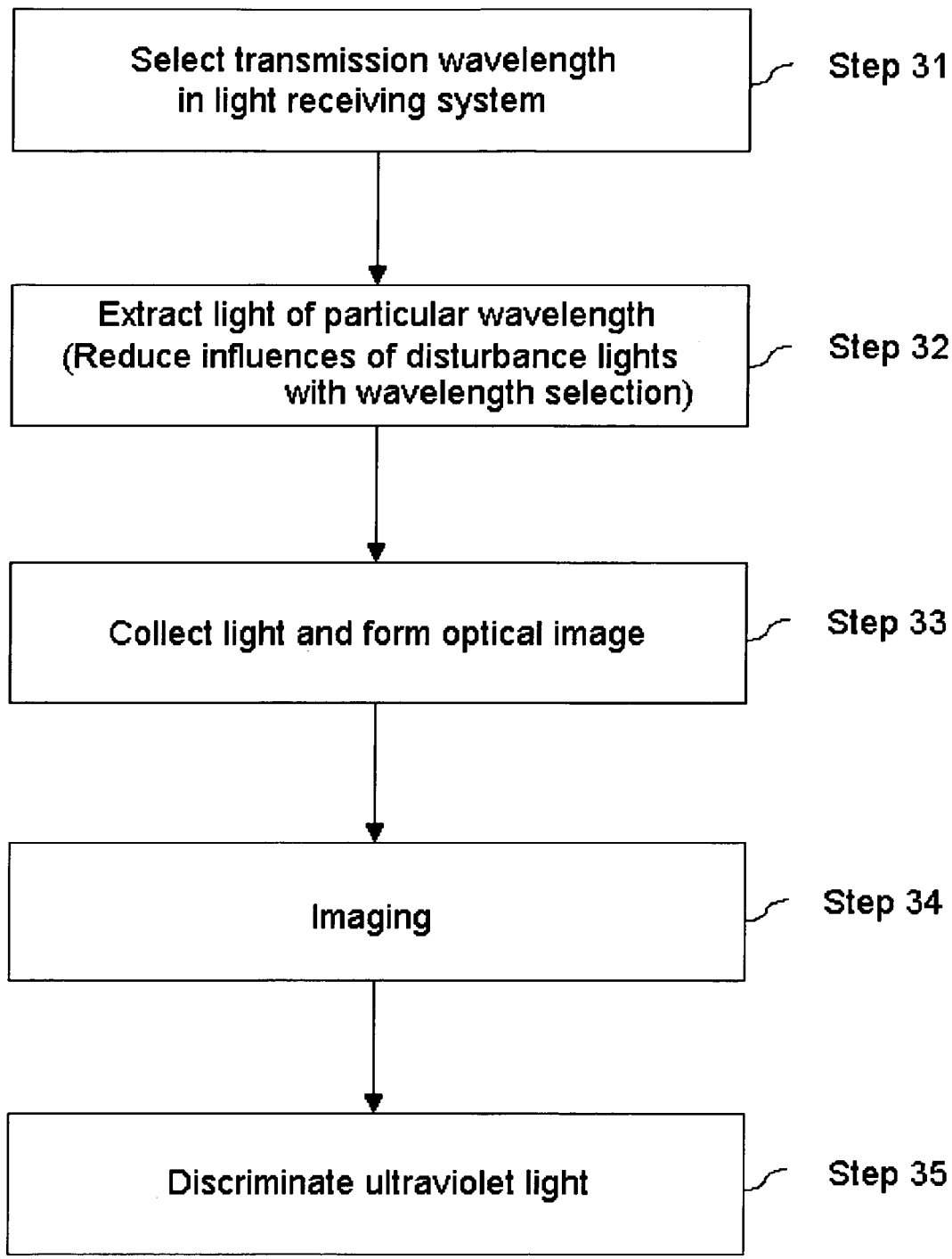
FIG. 4 is a flowchart showing an outline of a flame visualizing process according to the present invention.

The flame visualizing process according to the present invention is performed as shown in FIG. 4. First, to select the transmission wavelength in a light receiving system, an optical band-path filter is set so as to have the transmission wavelength center at each of wavelengths of OH-group emission spectrum lines (i.e., for a light of each wavelength of 280 nm or 309 nm), and to allow passage of the light of such each wavelength through the filter in a wavelength range of several nm (step 31). When the light receiving system is used in common with the leakage gas visualizing method, the optical band-path filter is switched over to an appropriate one. Then, only an ultraviolet light of the wavelength near 280 nm or 309 nm is extracted by the optical band-path filter (step 32). The ultraviolet light is collected by a light collecting optical system and converted into an electronic image, followed by amplifying the electronic image and converting it into an optical image again, whereby the optical image is formed (step 33). Then, the intensity of the ultraviolet light is converted into an electrical signal by an image pickup device, and the spatial intensity distribution of the ultraviolet light is obtained in the form of a visible image based on the recorded signal (step 34). The occurrence of a flame is detected depending on whether the spatial intensity distribution of the ultraviolet light exceeds a threshold (step 35).

Figure 5:
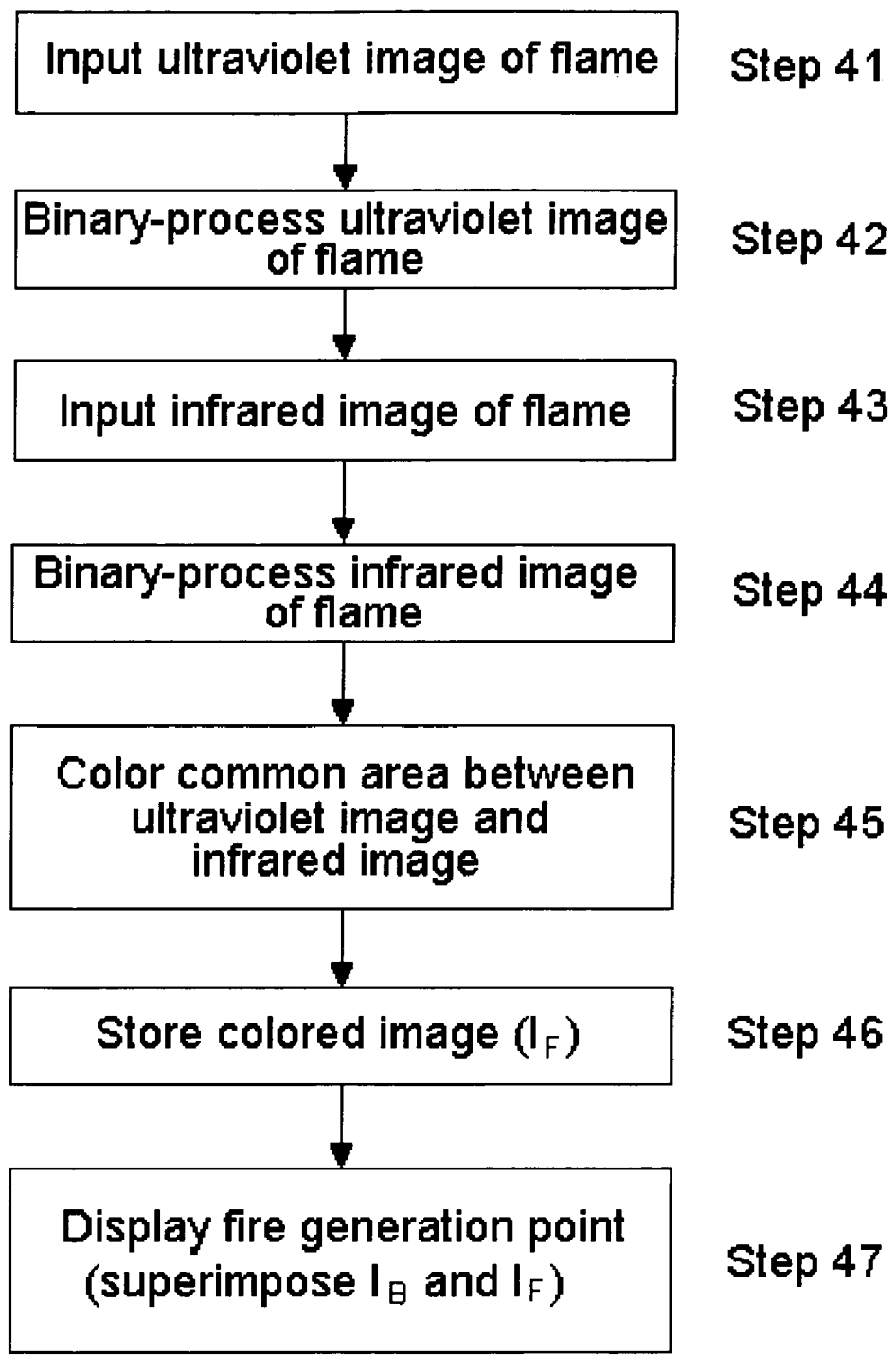
FIG. 5 is a flowchart of a process for locating a flame generation point according to the present invention.

The process for locating the flame generation point is performed as shown in FIG. 5. First, the ultraviolet image having been imaged in the step 34 is captured into the image processing system (step 41), and is subjected to binary processing to leave only areas of the ultraviolet image having values of not less than a threshold (step 42). Then, an infrared image is picked up by an infrared image pickup means such as a thermo-camera (step 43), and is subjected to binary processing to leave only areas of the infrared image having values of not less than a threshold (step 44). A common area (overlapped area) between the ultraviolet image and the infrared image both having been subjected to the binary processing is colored (step 45), and a resulting colored image is stored in the image processing system (step 46). Then, by superimposing the colored image with the background image $I_B$ stored in the step 22 (step 47), the fire generation point can be visualized.

Figure 6:
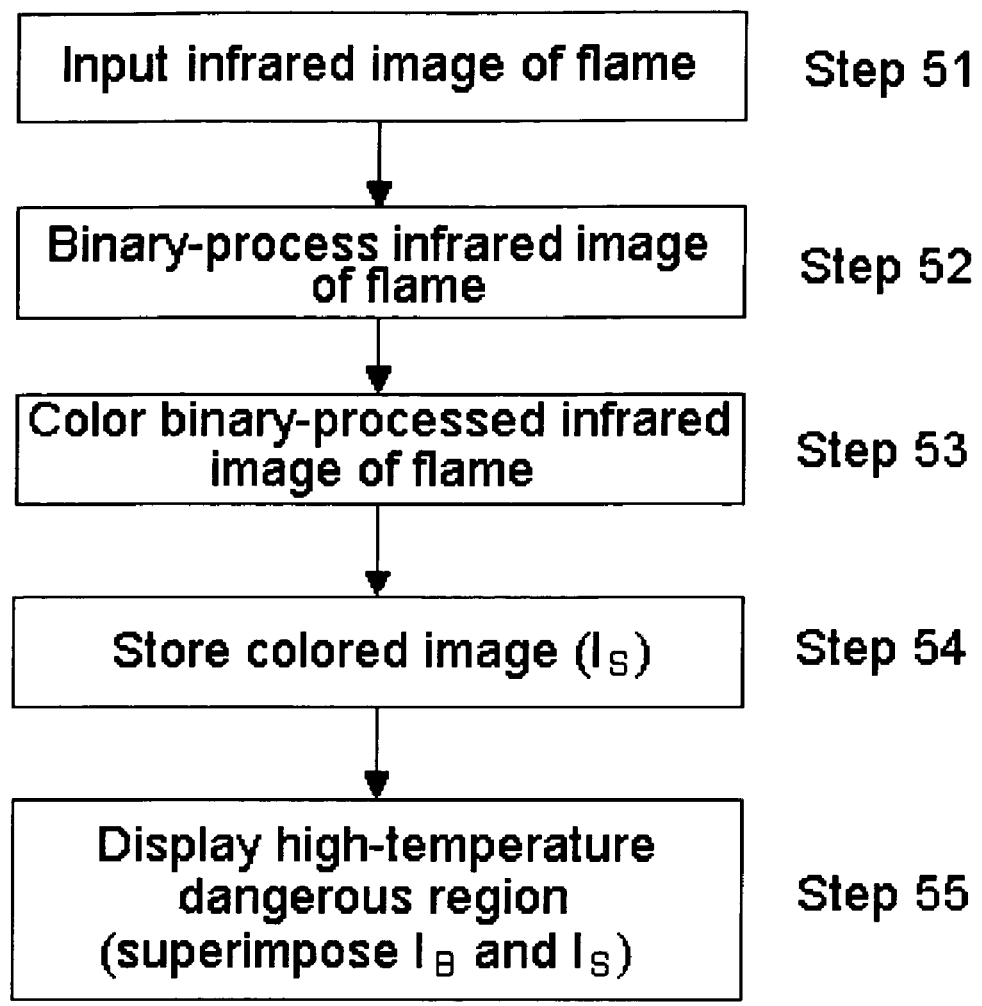
FIG. 6 is a flowchart of a process for locating a high-temperature dangerous region according to the present invention.

The process for locating a high-temperature dangerous region is performed as shown in FIG. 6. First, an infrared image is picked up by an infrared image pickup means such as a thermo-camera (step 51), and is subjected to binary processing to leave only areas of the infrared image having values of not less than a threshold (step 52). Then, the binary-processed infrared image is colored (step 53) and stored as a colored image $I_S$ in the image processing system (step 54). Then, by superimposing the colored image $I_S$ with the background image $I_B$, the high-temperature dangerous region can be visualized (step 55). The distance to the high-temperature dangerous region can be calculated based on triangular surveying when there are a plurality of image pickup means. Incidentally, when the infrared image binary-processed in the step 44 is employed in the step 53, the steps 51 and 52 are no longer required.

Figure 7:
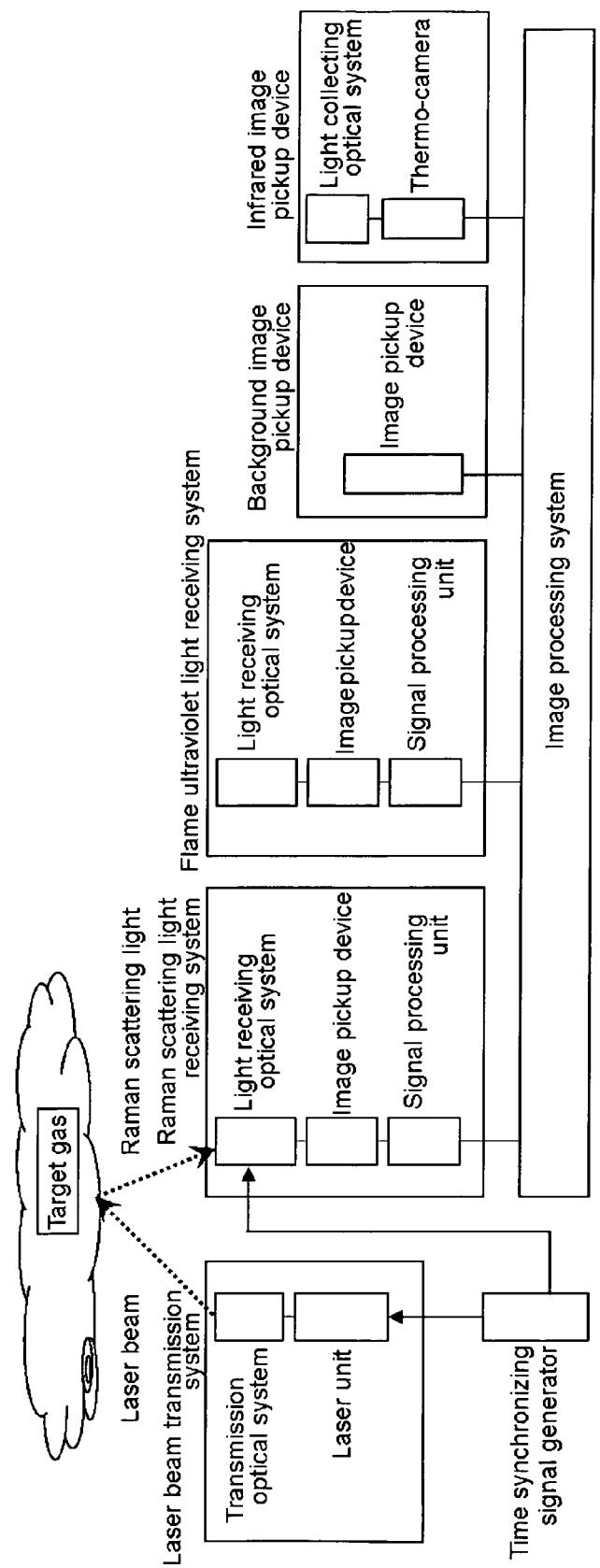
FIG. 7 is a block diagram showing the configuration of a gas leakage monitoring system according to the present invention.

FIG. 7 shows the configuration of a gas leakage monitoring system according to the present invention.

The gas leakage monitoring system according to the present invention comprises a laser beam transmission system, a Raman scattering light receiving system, a flame ultraviolet light receiving system, a time synchronizing signal generator, a background image pickup means, an infrared image pickup means, and an image processing system.

Among the above-mentioned components, those ones essential for detecting leakage gas are the "laser beam transmission system", the "Raman scattering light receiving system", and the "image processing system" (the "time synchronizing signal generator" is preferably also required from the viewpoint of eliminating noises, such as disturbance lights). Essential components for detecting a flame are the "flame ultraviolet light receiving system" and the "image processing system". To visualize a high-temperature dangerous region, the infrared image pickup means is further required. In the case of carrying out a part of the functions of the present invention, all the above-mentioned components are not necessarily required.

The laser beam transmission system comprises a laser unit and a transmission optical system for irradiating a laser beam to the space to be monitored. The transmission optical system may be constructed such that the laser beam is spread by a lens or the like for irradiation to the monitored space, or that the laser beam is scanned by a scanner or the like for irradiation to the monitored space.

The Raman scattering light receiving system comprises a light receiving optical system for selecting a light of the measurement wavelength from Raman scattering lights induced from the leakage gas upon irradiation of the laser beam by an optical band-path filter, and then collecting and focusing the selected Raman scattering light, an image pickup device for picking up an image focused by the light receiving system and converting the image into an electrical signal, and a signal processing unit for recording the electrical signal.

The flame ultraviolet light receiving system extracts only an ultraviolet light of the wavelength near 280 nm or 309 nm by an optical band-path filter, collects the extracted ultraviolet light by a light collecting optical system, and converts the collected ultraviolet light into an electrical image. After amplifying the electronic image and converting it into an optical image again, the optical image is formed.

To detect a flame by the Raman scattering light receiving system, an optical band-path filter having the transmission wavelength center at each of wavelengths of OH-group emission spectrum lines (i.e., for a light of each wavelength of 280 nm or 309 nm) must also be required in addition to the optical band-pass filter for selecting the Raman scattering light.

For that reason, in the case of detecting leakage gas and detecting a fire by one light receiving system, it is required to construct those optical band-pass filters in a switchable manner.

Figure 8A:
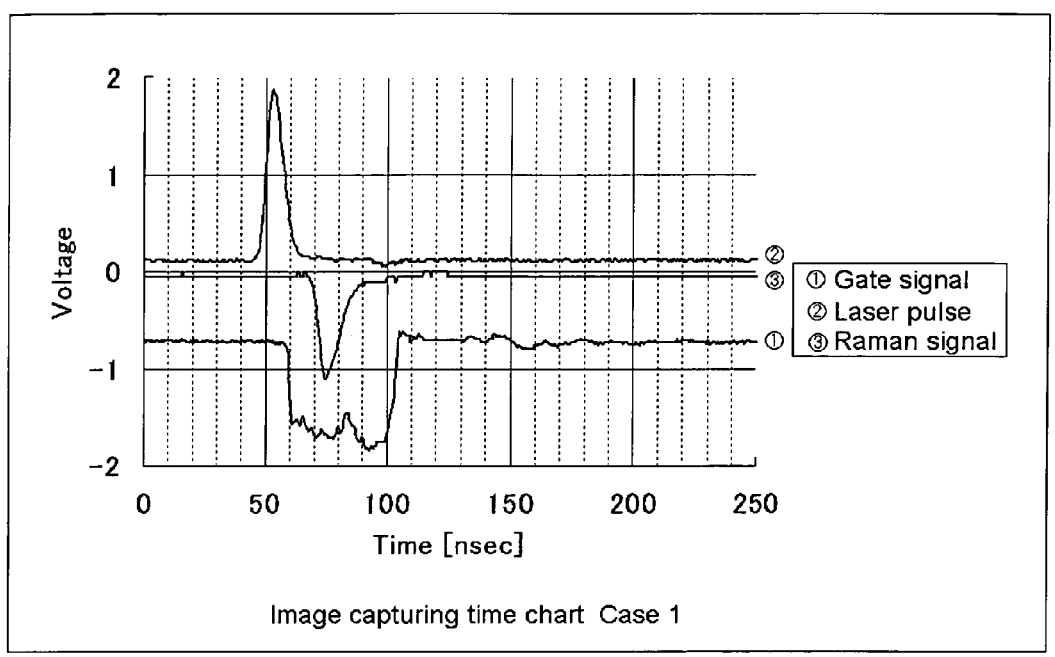
FIG. 8a is a time chart showing a Raman scattering light capturing (monitoring distance of 1.5 m-8 m).
Figure 8B:
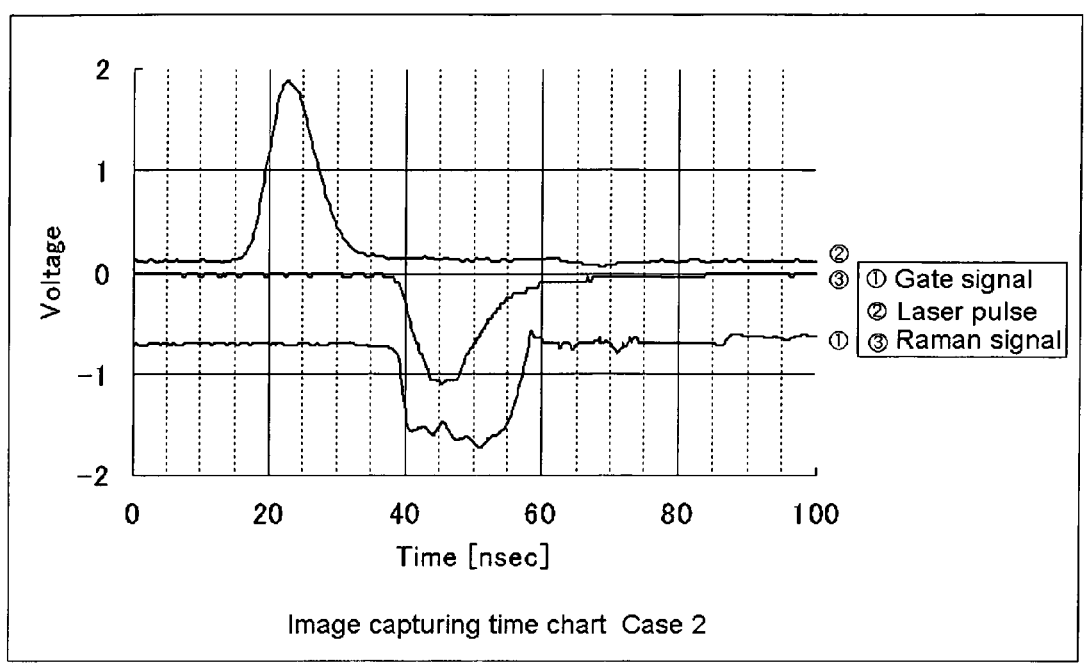
FIG. 8b is a time chart showing a Raman scattering light capturing (monitoring distance of 3 m-6 m).

The time synchronizing signal generator is connected to both the laser unit and the light receiving optical system of the Raman scattering light receiving system, and generates a reference signal for holding the timing of irradiating the laser beam to the monitored space and the timing of starting and ending the reception of the Raman scattering light in synchronized relation. The timing of irradiating the laser beam and the timing of receiving the Raman scattering light differ depending on the distance to the target gas to be monitored. For example, when the distance to the monitoring target is in the range of about 1.5 m to 8 m, the process is performed in accordance with such a time chart (FIG. 8*a*) that, because of the light velocity being about 30 cm/1 nano second, image capturing is started with a delay of 10 nano seconds after the irradiation of the laser beam and is continued for a time of 45 nano seconds. When the distance to the monitoring target is in the range of about 3 m to 6 m, the process is performed in accordance with such a time chart (FIG. 8*b*) that image capturing is started with a delay of 20 nano seconds after the irradiation of the laser beam and is continued for a time of 20 nano seconds.

The background image pickup means is an image pickup means, such as a CCD camera, and picks up a background image for locating the leakage gas and/or the flame position.

The infrared image pickup means comprises a light collecting optical system for collecting a thermal spectrum, and an image pickup means, such as a thermo-camera. Then, the infrared image pickup means picks up an infrared image for locating a high-temperature dangerous region.

The image processing system includes a processing program for imaging the detected signal.

The present invention will be described below in more detail in connection with examples of the gas leakage monitoring method and system according to embodiments of the present invention. It is to be noted that the present invention is in no way limited by the following embodiments.

Embodiment 1

Figure 9:
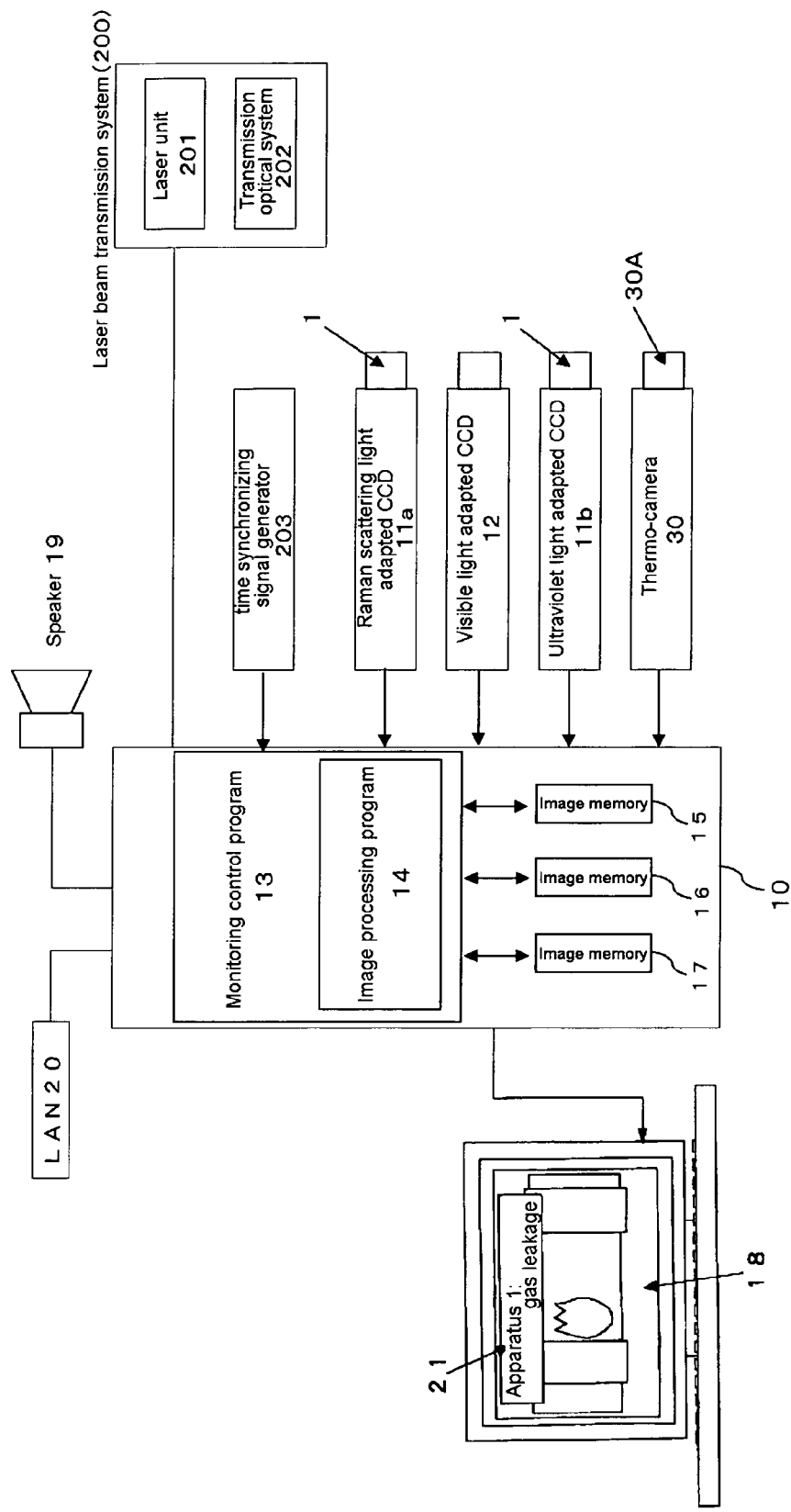
FIG. 9 is a block diagram showing the configuration of a gas leakage monitoring system according to Embodiment 1.

FIG. 9 shows one example the configuration of a gas leakage monitoring system according to Embodiment 1.

The system of Embodiment 1 is able to monitor leakage gas, locate a gas leakage point, monitor a flame, and to visualize a high-temperature dangerous region.

Referring to FIG. 9, numeral 10 denotes a personal computer including an image processing program. Connected to the personal computer 10 are a time synchronizing signal generator 203 and a Raman scattering light adapted camera 11*a* both serving as a leakage gas image pickup means, a visible light adapted camera 12 serving as a background image pickup means, an ultraviolet light adapted camera 11b serving as a flame image pickup means, and a thermo-camera 30 serving as an infrared image pickup means via cables.

Image pickup targets of the Raman scattering light adapted camera 11a and the ultraviolet light adapted camera 11b are set to the monitoring target. When an optical band-pass filter 3 is constructed in a switchable manner, the Raman scattering light adapted camera 11a and the ultraviolet light adapted camera 11b can be mounted in the same housing.

The visible light adapted camera 12 and the thermo-camera 30 are each provided with a wide-angle lens so as to pickup an image of the background with lights in a wavelength range not containing the Raman scattering light over a wide region including the monitoring target.

Numeral 200 denotes a laser beam transmission system comprising a laser unit 201 and a transmission optical system 202. The laser beam transmission system two-dimensionally irradiates a pulsing laser beam to an area to be monitored.

The irradiation of the laser beam can be turned on/off by controlling the laser unit from the personal computer via a cable, or by issuing/cutting a signal outputted from the time synchronizing signal generator 203.

Figure 10:
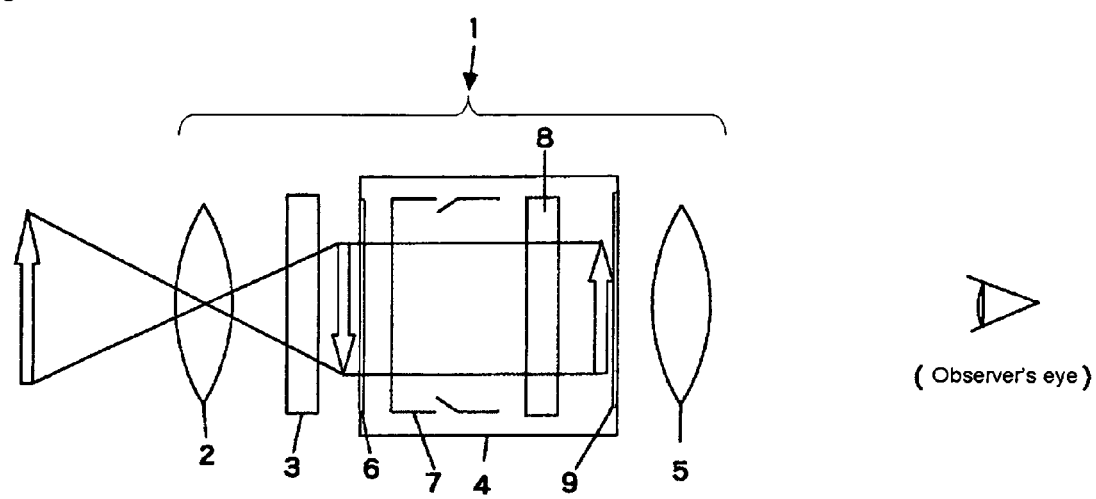
FIG. 10 is a block diagram showing the configuration of a light receiving optical system according to Embodiment 1.

Numeral 1 denotes each light receiving optical system 1 that serves as an image pickup means according to Embodiment 1. As shown in FIG. 10, the light receiving optical system 1 comprises an objective lens 2 serving as a light collecting optical system, an optical band-pass filter 3 serving as a transmission light selecting means, an image intensifier 4 serving as an ultraviolet light amplifying/visualizing means, and an eyepiece 5.

The objective lens 2 comprises a condenser lens, a relay lens, and a lens barrel (not shown) so that an image of the observation target can be formed on an imaging surface of the image intensifier 4.

The image intensifier 4 comprises a photoelectric surface 6 formed of a thin film disposed on the side facing the optical band-pass filter 3 and having the external photoelectric effect, an electronic lens 7, a micro-channel plate 8, and a fluorescent surface 9. An ultraviolet light having passed through the optical band-pass filter 3 is converted into an electronic image by the photoelectric surface 6. The electronic image is focused by the electronic lens 7 and is subjected to secondary electron amplification by the micro-channel plate 8. Then, the amplified electronic image is returned to an optical image again by the fluorescent surface 9. In this way, a weak Raman scattering light from leakage gas and an ultraviolet light from a flame are converted into visible images.

Incidentally, the optical band-pass filter 3 and the objective lens 2 can be reversed in order of arrangement from the illustrated one.

The optical band-pass filter 3 of the Raman scattering light adapted camera 11a has the center of transmission wavelength for observing the wavelength of the Raman scattering light from the gas to be monitored. The central wavelength for each kind of gas to be monitored is as shown in Table 1 given above.

Figure 11:
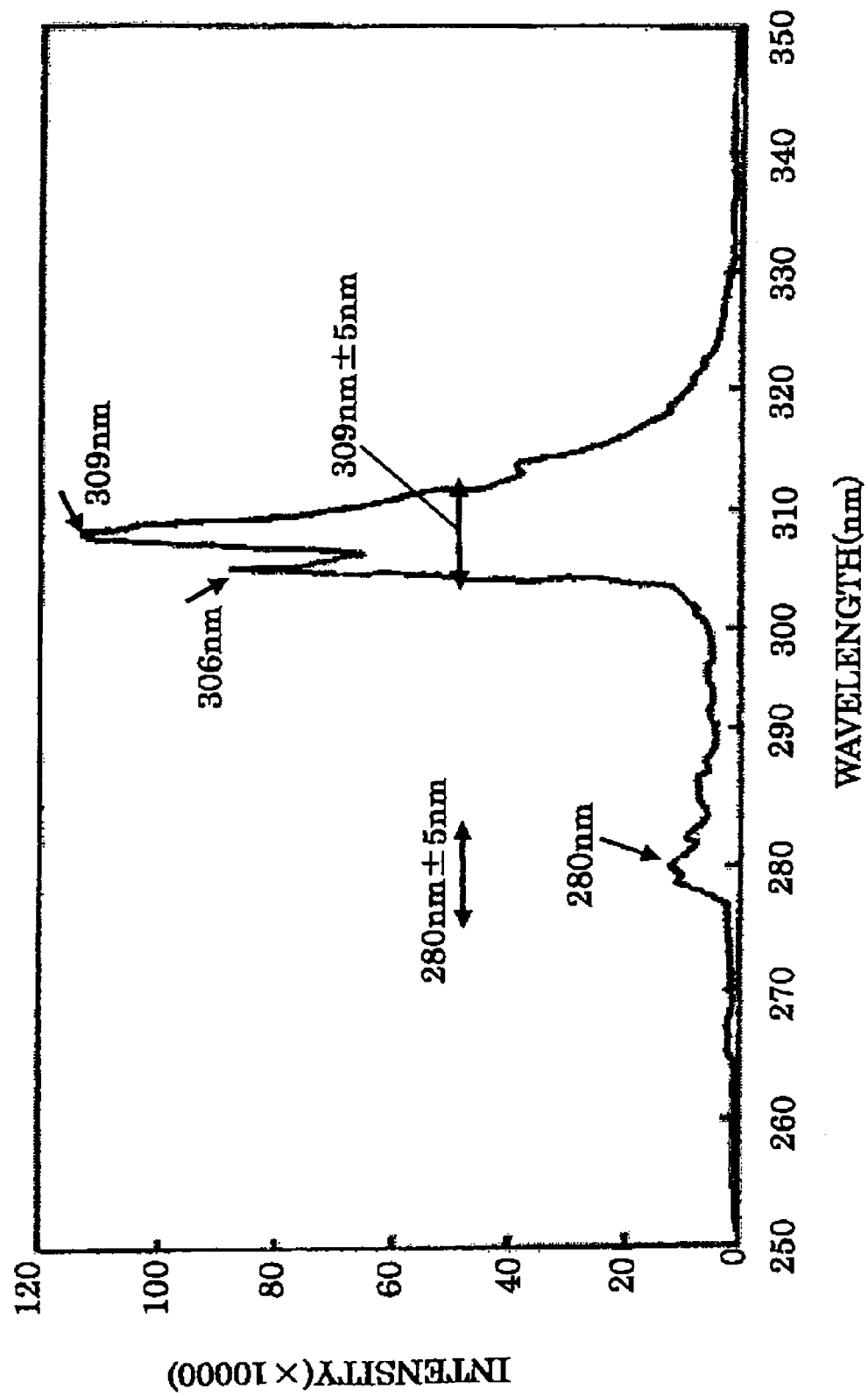
FIG. 11 is a graph showing an emission spectrum of a hydrogen flame.

The optical band-pass filter 3 of the ultraviolet light adapted camera 11b has the center of transmission wavelength for a light of each wavelength 280 nm or 309 nm and also has a transmission wavelength width within a half width at half maximum of 5 nm. For example, the emission spectrum of a hydrogen flame has, as shown in FIG. 11, an emission region centered at the wavelength of 280 nm and an emission region centered at the wavelength of 309 nm. By making the emission spectrum of a hydrogen flame transmitted through the optical band-pass filter 3, therefore, an ultraviolet light having a wavelength range of 280 nm±5 nm or a wavelength range of 309 nm±5 nm is allowed to pass through the filter, while lights of other wavelengths are cut off.

Although this embodiment uses the optical band-pass filter 3 described above, it is desirable to use a filter having a narrower transmission wavelength width from the viewpoint of lessening disturbance influences, such as sunlight and other illumination. For that reason, a band-pass filter having a transmission wavelength range with a full width at half maximum of 1.5 nm is preferably used. By using such a band-pass filter having a transmission wavelength range with a full width at half maximum of 1.5 nm, disturbance lights can be reduced and the flame can be more clearly observed than the case of using a band-pass filter having a wider transmission wavelength range. On the other hand, widening the transmission width of the transmission wavelength range leads to an advantage that a background image can be captured along with a flame image and the visible light adapted camera 12 can be omitted.

A Raman scattering light is generated based on a phenomenon induced upon irradiation of a laser beam. For example, when a high-speed pulsing laser beam is irradiated, the Raman scattering light is also generated in the form of a high-speed pulse. By measuring the pulsing Raman scattering light in time synchronized relation to the laser irradiation, the Raman scattering light can be discriminated from disturbances, such as sunlight and other illumination lights which moderately vary with time, and a sharper gas distribution image can be observed.

In the light receiving optical system of the Raman scattering light adapted camera 11a, a voltage applied to the electronic lens 7 of the image intensifier 4 is controlled in sync with the irradiation pulse of the laser beam to turn on/off arrival of electrons to the micro-channel plate 8. The light reception is thereby allowed or inhibited so as to amplify only the light in a time zone in which the Raman scattering light is emitted (i.e., a time zone in which the laser beam is irradiated) by the micro-channel plate 8. With such gate-on/off operation, it is possible to minimize influences of disturbances, such as sunlight, other illumination lights, and laser induced fluorescence from the monitored area.

The visible image formed on the fluorescent surface 9 of the image intensifier 4 of course can be picked up by the Raman scattering light adapted camera 11a and the ultraviolet light adapted camera 11b, and visually observed even by the naked eye through the eyepiece 5.

The thermo-camera 30 serving as an infrared image pickup means comprises a light collecting optical system 30A for collecting a heat spectrum due to black body radiation emitted from air, vapor, piping equipment, etc. around a flame, which are heated by the flame, an optical band-pass filter serving as a transmission light selecting means that allows transmission of a light of 7 µm-14 µm through the filter to select the heat spectrum collected by the light collecting optical system 30A, and an image receiving surface on which an infrared image of the heat spectrum selected by the optical band-pass filter is formed. With that construction, the thermo-camera 30 converts the infrared image of a flame into an electrical signal.

The light collecting optical system 30A comprises an objective lens, a relay lens, and a lens barrel so that an image of the observation target can be formed on an image receiving surface of the thermo-camera 30.

The infrared light having passed through the light collecting optical system 30A and the optical band-pass filter is converted into an electronic image by the thermo-camera 30 and then converted into a visible image. The infrared image representing an infrared light distribution region captured by the thermo-camera 30 can also be visually observed by the naked eye through an eyepiece lens system.

The personal computer 10 is connected to the Raman scattering light adapted camera 11a, the ultraviolet light adapted camera 11b, the visible light adapted camera 12, and a LAN 20, and contains a monitoring control program 13 for executing monitoring control. The monitoring control program 13 includes an image processing program 14 for controlling image processing executed in the Raman scattering light adapted camera 11a, the ultraviolet light adapted camera 11b, the visible light adapted camera 12, and the thermo-camera 30.

Then, an image processing means in this Embodiment 1 is made up of the personal computer 10, the monitoring control program 13, the image processing program 14, an input means (not shown) such as a keyboard or a mouse, and a monitor screen 18.

When gas of the measurement target is detected or when a flame is detected, the monitoring control program 13 issues an alarm through a speaker 19 or informs the detected fact to the other component, e.g., the personal computer via the LAN 20. Also, when gas of the measurement target is detected or when a flame is detected, the monitoring control program 13 gives warnings of the place under monitoring or the position of an apparatus monitored and the occurrence of an abnormality in the form of characters and voices.

The image processing program 14 is able to display the images picked up by the Raman scattering light adapted camera 11a and the ultraviolet light adapted camera 11b, the background image picked up by the visible light adapted camera 12, and the infrared image picked up by the thermo-camera 30 on one monitor screen 18 at the same time in any desired combination. Also, the background image picked up by the visible light adapted camera 12, the infrared image picked up by the thermo-camera 30, and the images picked up by the Raman scattering light adapted camera 11a and the ultraviolet light adapted camera 11b can be displayed in superimposed relation to each other in any desired combination.

By way of example, the image picked up by the Raman scattering light adapted camera 11a can be displayed in superimposed relation to the visible image picked up by the visible light adapted camera 12 through the steps of combining the visible image picked up by the visible light adapted camera 12 and the image picked up by the Raman scattering light adapted camera 11a with each other, which are outputted respectively to image memories 15, 16 in a video board of the personal computer 10, storing a composite image in an image memory 17, and outputting the composite image to the monitor screen 18 so that both the images can be recognized at the same time.

Next, a flow of processing executed in the gas leakage monitoring system of this Embodiment 1 is shown in FIGS. 12a through 12d.

Figure 12A:
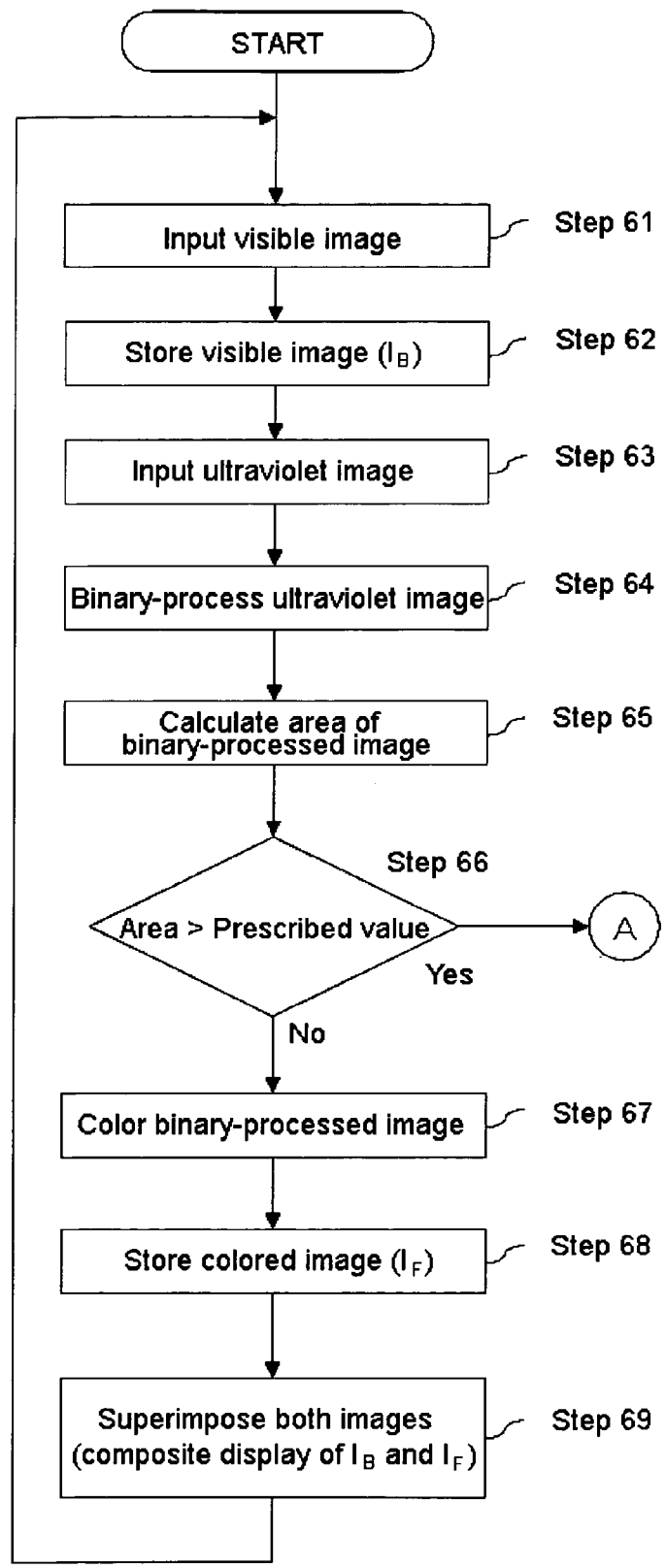
FIG. 12a is a flowchart (1/4) of the processing executed in the gas leakage monitoring system according to Embodiment 1.

As shown in the flowchart of FIG. 12a, when monitoring control is started (START), the background image (visible image) is first picked up by the visible light adapted camera 12 (step 61). The picked-up background image is stored as a visible image ($I_B$) in accordance with the image processing program 14 (step 62). Then, an ultraviolet image of a target area for detection of leakage gas is picked up by the Raman scattering light adapted camera 11a (step 63). The ultraviolet image picked up by the Raman scattering light adapted camera 11a is subjected to binary processing in accordance with the image processing program 14 (step 64). In this binary processing, the ultraviolet image is compared with a preset threshold, and a value of not less than the threshold is determined as indicating the target gas. The image processing program 14 calculates an area of the binary-processed image (i.e., the Raman scattering intensity) (step 65).

The image processing program 14 compares the calculated Raman scattering intensity (i.e., the Raman spectrum intensity) with a prescribed value set in advance (step 66). This prescribed value is previously set in accordance with the monitoring control program 13 or during initial setting of the image processing program 14, for example, in an adjustable manner.

If the Raman scattering intensity does not exceed the prescribed value, the image processing program 14 colors the binary-processed image (step 67), stores a colored image $I_F$ (step 68), and displays the colored image $I_F$ and the background image $I_B$ on the screen 18 in superimposed relation (step 69). A display time of the composite image can be set at any desired interval, e.g., 10 seconds or 1 minute, which is optionally adjustable in accordance with the monitoring control program 13 or the image processing program 14. Then, after the lapse of a predetermined time, the control flow returns to a point upstream of the step 61 for the continued monitoring of the target area.

Figure 12B:
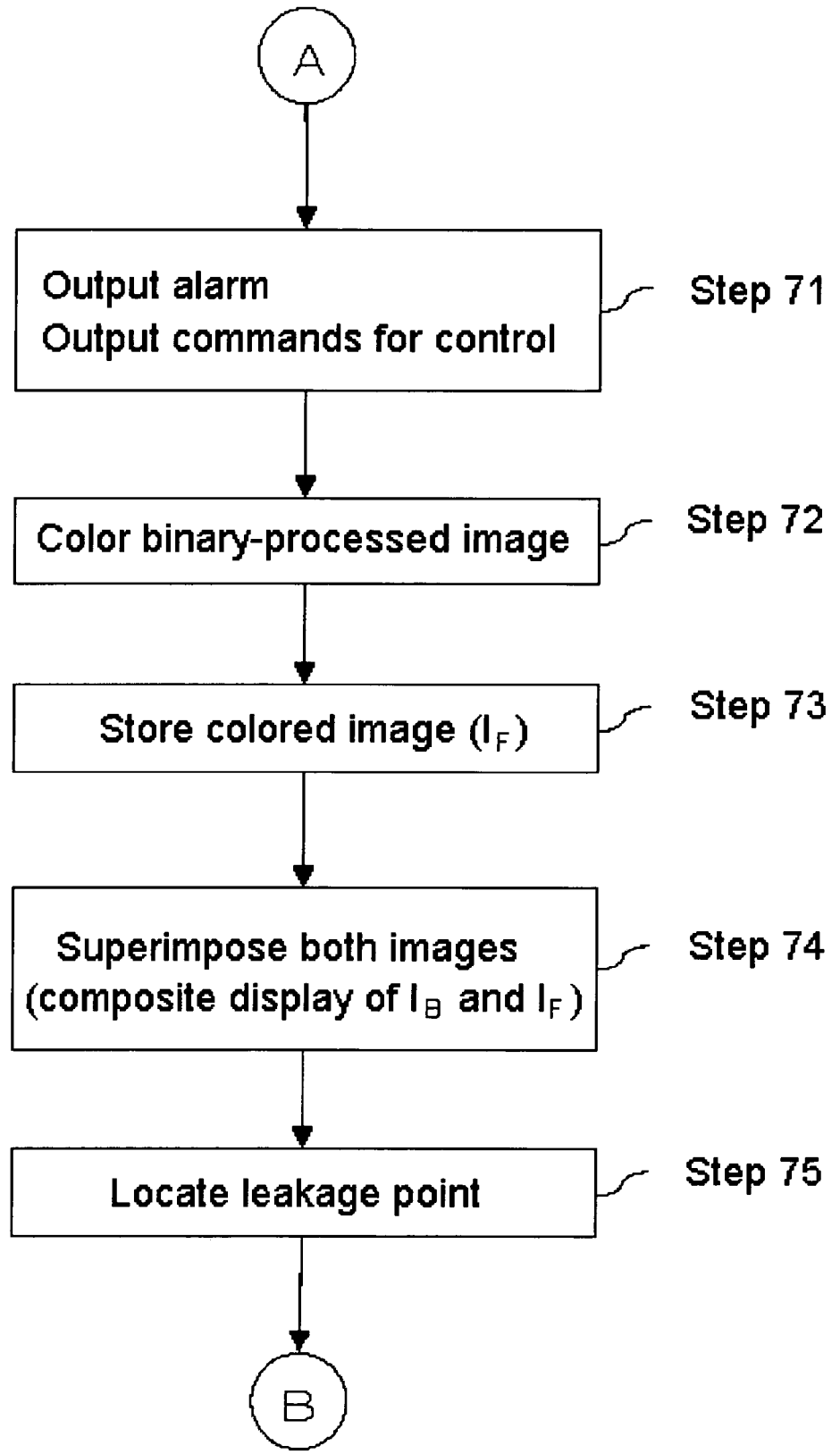
FIG. 12b is a flowchart (2/4) of the processing executed in the gas leakage monitoring system according to Embodiment 1.
Figure 12C:
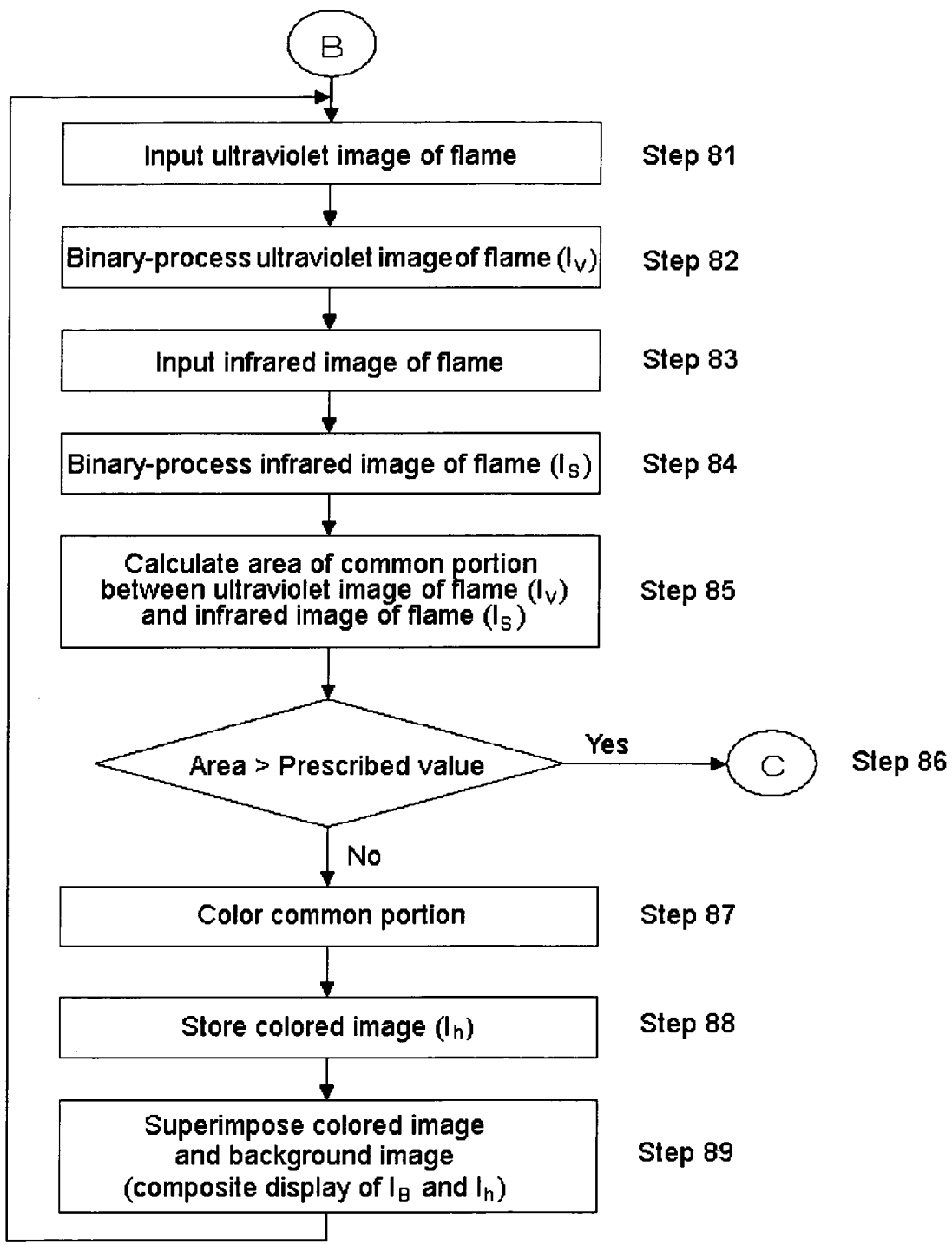
FIG. 12c is a flowchart (3/4) of the processing executed in the gas leakage monitoring system according to Embodiment 1.

If the Raman scattering intensity exceeds the prescribed value, the image processing program 14 determines that the target gas is leaked, followed by executing the processing shown in FIG. 12b. More specifically, the image processing program 14 transmits commands to the monitoring control program 13 so as to make such emergent actions as issuing an alarm through the speaker 19, stopping the supply of gas, and/or sprinkling water to suppress a temperature rise caused upon firing (step 71). Additionally, the gas leakage monitoring system may be constructed by installing an alarm unit and communication equipment such that, when the ultraviolet ray of the Raman scattering light from the target gas is detected on the photoelectric surface 6 or when an image of the target gas is imaged on the fluorescent surface 9, an alarm is automatically issued in response to a detected signal of such an image.

Subsequently, the image processing program 14 colors the binary-processed image (step 72), stores a colored image $I_F$ (step 73), and displays the colored image $I_F$ and the background image $I_B$ on the screen 18 in superimposed relation, thereby visualizing the leakage gas (step 74). The distance to the leakage gas is calculated based a time lapsed from the irradiation of the laser beam to arrival of the Raman scattering light, thereby locating the leakage point (step 75).

If there occurs gas leakage, the occurrence of a flame is monitored in succession. As shown in a flowchart of FIG. 12c, when monitoring of a flame is started, an ultraviolet image of the target area for gas leakage detection is first picked up by the ultraviolet light adapted camera 11b (step 81). The picked-up ultraviolet image of a flame is subjected to binary processing in accordance with the image processing program 14 (step 82). Subsequently, an infrared image is picked up by the infrared light image pick-up means, such as the thermo-camera (step 83), and is subjected to binary processing in accordance with the image processing program 14 (step 84). Then, the image processing program 14 calculates an area of a common portion (overlapped portion) between the ultraviolet image and the infrared image each having been binary-processed image (step 85).

If the area of the common portion does not exceed the prescribed value, the image processing program 14 colors the common portion (step 87), superimposes the colored image $I_h$ and the background image $I_B$ with each other (step 88), and displays both the images on the screen 18 (step 89). A display time of the composite image can be set at any desired interval of, e.g., 10 seconds or 1 minute, which is optionally adjustable in accordance with the monitoring control program 13 or the image processing program 14. Then, after the lapse of a predetermined time, the control flow returns to a point upstream of the step 81 for the continued monitoring of the target area.

Figure 12D:
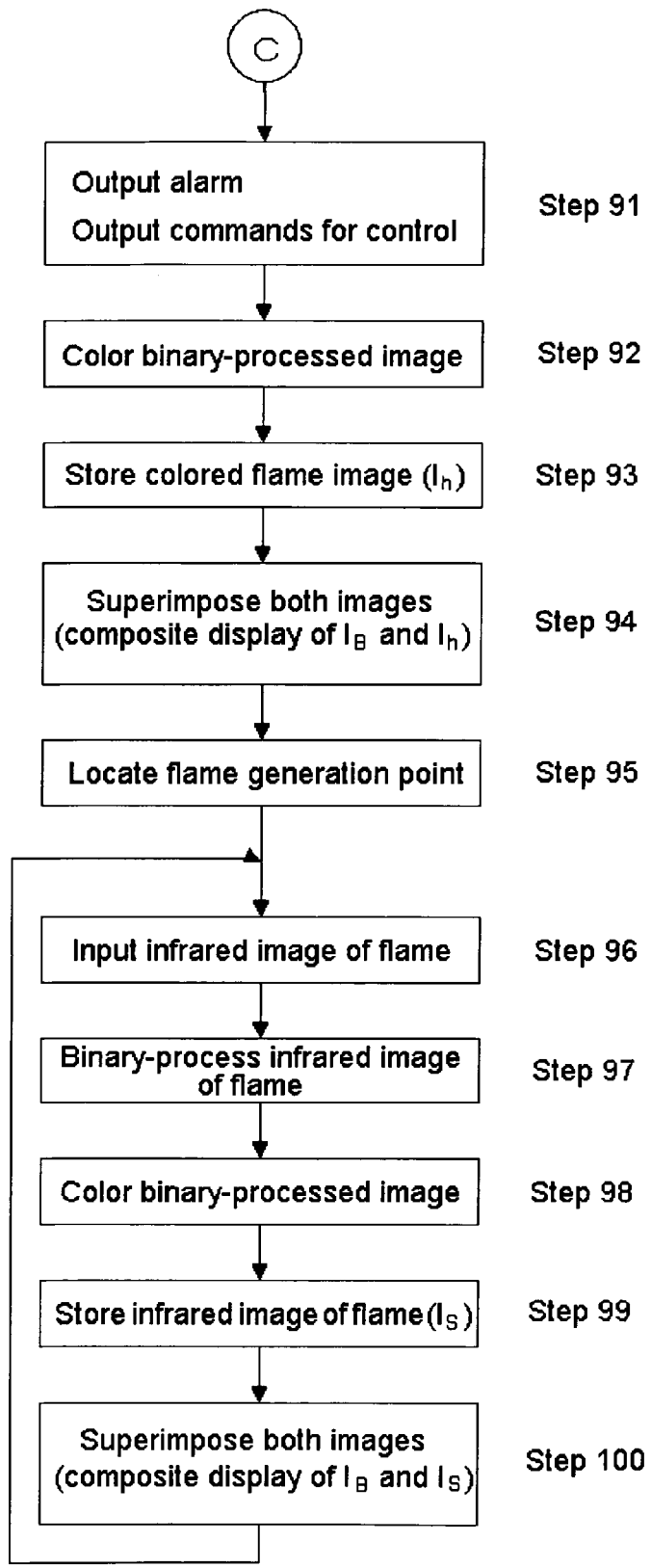
FIG. 12d is a flowchart (4/4) of the processing executed in the gas leakage monitoring system according to Embodiment 1.

If the area of the common portion exceeds the prescribed value, the image processing program 14 determines that there has occurred a flame, followed by executing the processing shown in FIG. 12*d*. More specifically, the image processing program 14 transmits commands to the monitoring control program 13 so as to make such emergent actions as issuing an alarm through the speaker 19 and/or operating a sprinkler (step 91). Additionally, the gas leakage monitoring system may be constructed by installing an alarm unit and communication equipment such that, when the ultraviolet image of the flame is formed on the photoelectric surface 6 or when a flame image is formed on the fluorescent surface 9, an alarm is automatically issued in response to a detected signal of such an image. Subsequently, the image processing program 14 colors the binary-processed flame image (step 92), stores a colored image $I_h$ (step 93), and superimposes the colored image $I_h$ and the background image $I_B$ with each other (step 94), thereby displaying both the images on the screen 18. As a result, the flame is visualized and the flame generation point is located (step 95).

Locating a high-temperature dangerous region will be described below. As shown in a flowchart of FIG. 12*d*, after locating the flame generation point, an infrared image of the flame detected region is picked up by the thermo-camera 30 (step 96). The picked-up infrared image is subjected to binary processing in accordance with the image processing program 14 (step 97). In this binary processing, the infrared image is compared with a preset threshold, and a pixel having a value of not less than the threshold is determined as indicating the high-temperature dangerous region. The image processing program 14 colors the binary-processed image (step 98) and stores a colored image $I_S$ (step 99). Then, the colored image $I_S$ picked up by the thermo-camera 30 and the background image $I_B$ are superimposed with each other and displayed on the screen 18 (step 100). A display time of the composite image can be set at any desired interval, e.g., 10 seconds or 1 minute, which is optionally adjustable in accordance with the monitoring control program 13 or the image processing program 14. Then, after the lapse of a predetermined time, the control flow returns to a point upstream of the step 96 for the continued monitoring of the target area until a monitoring stop command is issued.

[Effect of Embodiment 1]

With the leakage gas monitoring system, as described above, since the light receiving optical system 1 converts the target gas into a visible image and the image processing program 14 displays the target gas and the background image through combination processing, it is possible to visually confirm a leakage of the target gas and/or the situation in generation of a flame and/or the high-temperature dangerous region.

Also, since the monitoring control program 13 has at least one of the function of issuing an alarm from the speaker 19 or a buzzer and the function of sending information or communicating a notice via the LAN 20 when the light receiving optical system 1 has detected the target gas F, the occurrence of an emergent state can be notified at once. As a matter of course, the keyboard or the mouse (not shown) can be used to control the monitoring control program 13, the image processing program 14, and other programs when plural sets of the Raman scattering light adapted cameras 11*a*, the ultraviolet light adapted cameras 11*b*, the visible light adapted cameras 12, and the thermo-cameras 30 are connected to the personal computer 10.

When a wide area or a plurality of places are to be monitored, the monitoring can be performed by connecting each set of the Raman scattering light adapted camera 11*a*, the ultraviolet light adapted camera 11*b*, the visible light adapted camera 12, the thermo-camera 30 and so on to a network. In this case, if the light receiving optical system 1 installed in any of the places detects the target gas F, the image processing program 14 displays the position where the target gas F has been generated, i.e., the position of the occurrence of a leakage of the target gas and/or the flame on the monitor screen 18 (position display means), in accordance with a signal identifying the light receiving optical system 1 that has detected the target gas F.

Such display 21 of the occurrence of a leakage of the target gas and/or the generation position of a flame displays the background image and blinking large-sized preset characters on the monitor screen 18. It is therefore possible to certainly recognize the target leakage point and to take operations for stopping supply of the target gas and preventing the spread of a fire.

Further, the monitoring control program 13 can record the position of each light receiving optical system 1, characters and voices as specific information in advance, and can display the leakage point on the screen or announcing it with voices through local area broadcasting in accordance with ID information (information for identifying each light receiving optical system 1) transmitted from the light receiving optical system 1 when a leakage of the target gas is detected.

In addition, when the light receiving optical system 1 has detected the target gas F, the monitoring control program 13 can also close a target gas supply valve near the leakage point of the target gas F or sprinkle water from a distinguishing means, such as a fireplug, in accordance with the identification information of the light receiving optical system 1 that has detected the target gas F.

According to the gas leakage monitoring system constructed as described above, even when leakage gas is invisible to the naked eye, the leakage gas can be visually recognizable with the naked eye, and therefore monitoring of colorless and transparent gas can be realized in a space to be monitored. By using an electronic image pickup means instead of the visual monitoring with the naked eye, it is possible to electrically capture respective images of the target gas and/or the flame and/or the high-temperature dangerous region.

Embodiment 2

Figure 13:
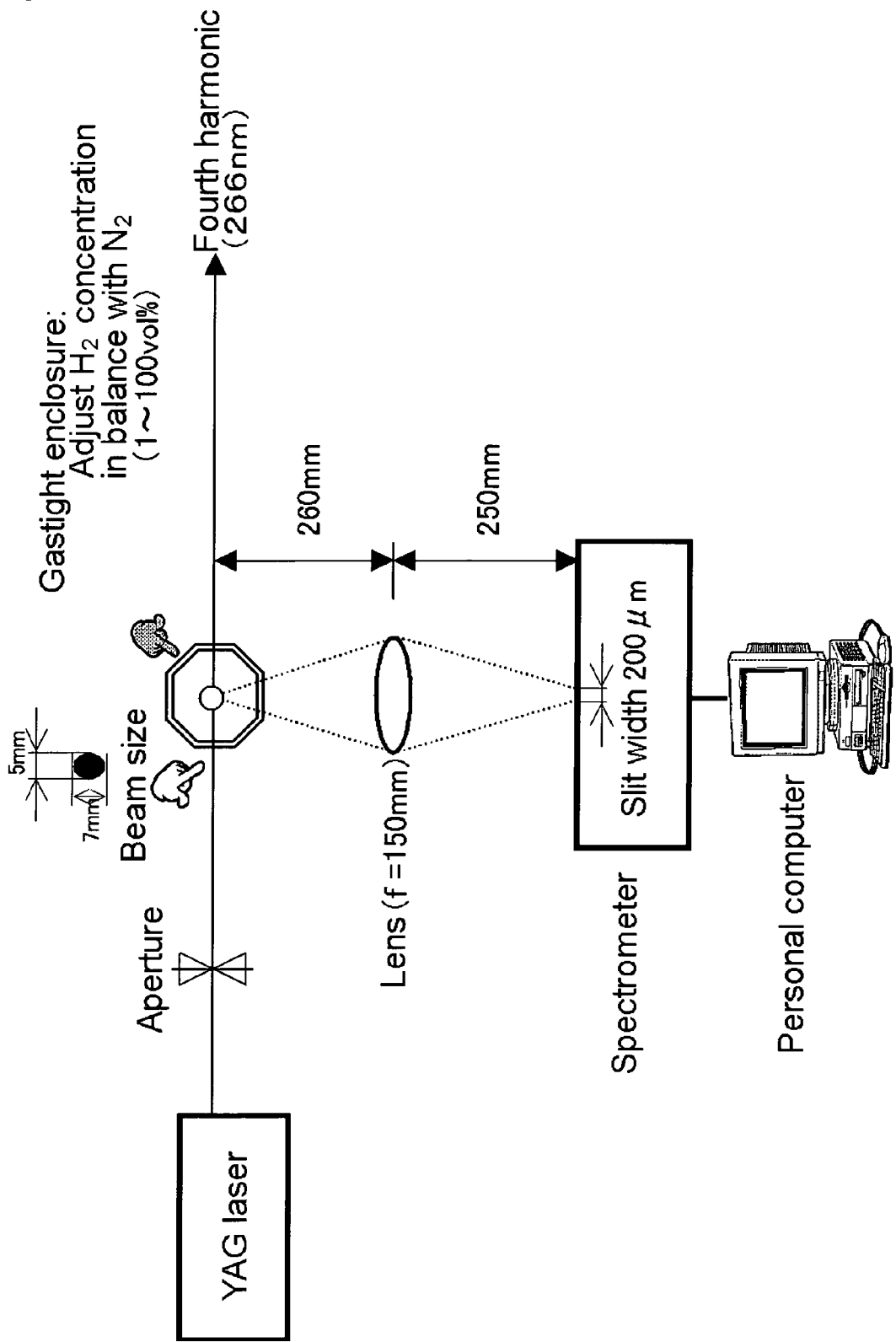
FIG. 13 is a schematic diagram showing an experimental system according to Embodiment 2 in which hydrogen is used as target gas.

FIG. 13 is a schematic diagram showing an experimental system in which hydrogen is used as the target gas.

Figure 14:
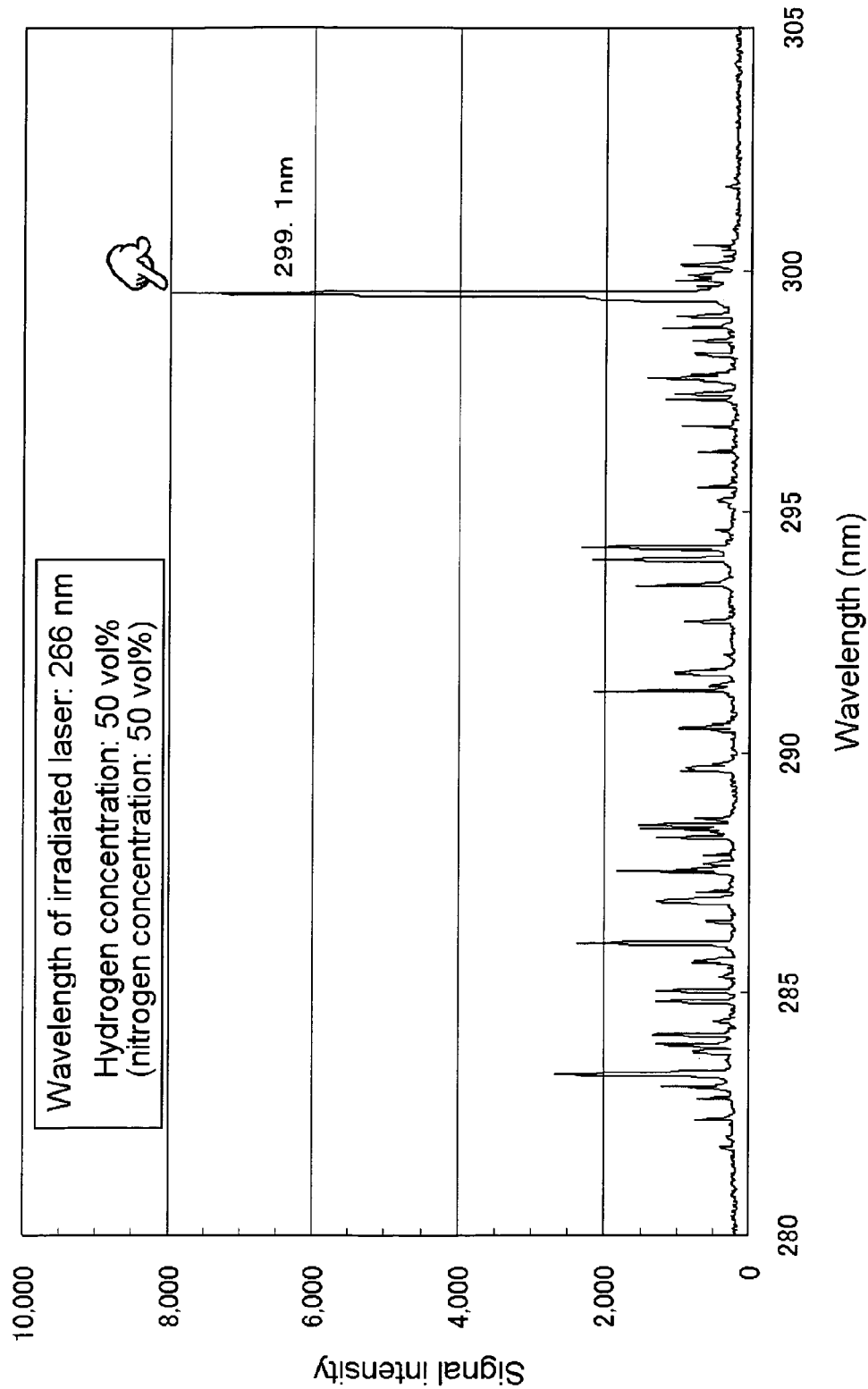
FIG. 14 is a graph showing the spectrum of a Raman scattering light emitted from hydrogen according to Embodiment 2.

An experiment was conducted by employing the system configuration shown in FIG. 13, hydrogen gas as the target gas, and a 266-nm fourth harmonic of a YAG laser as the laser beam source. As a result, as shown in FIG. 14, the Raman scattering spectrum emitted from the hydrogen gas has an emission region about a wavelength 299.1 nm being as the center. Correspondingly, the optical band-pass filter 3 has the transmission wavelength center for a light having a wavelength of 299.1 nm and its transmission wavelength range has a half width at half maximum of 1 nm. Thus, the optical band-pass filter allows an ultraviolet light having a wavelength range of 299.1 nm±1 nm to pass through the filter, and cuts off lights of other wavelengths. When strong fluorescence is generated in an environment for measuring the Raman scattering light, the measurement can also be made using the Raman scattering light shifted toward the shorter wavelength side.

Figure 15:
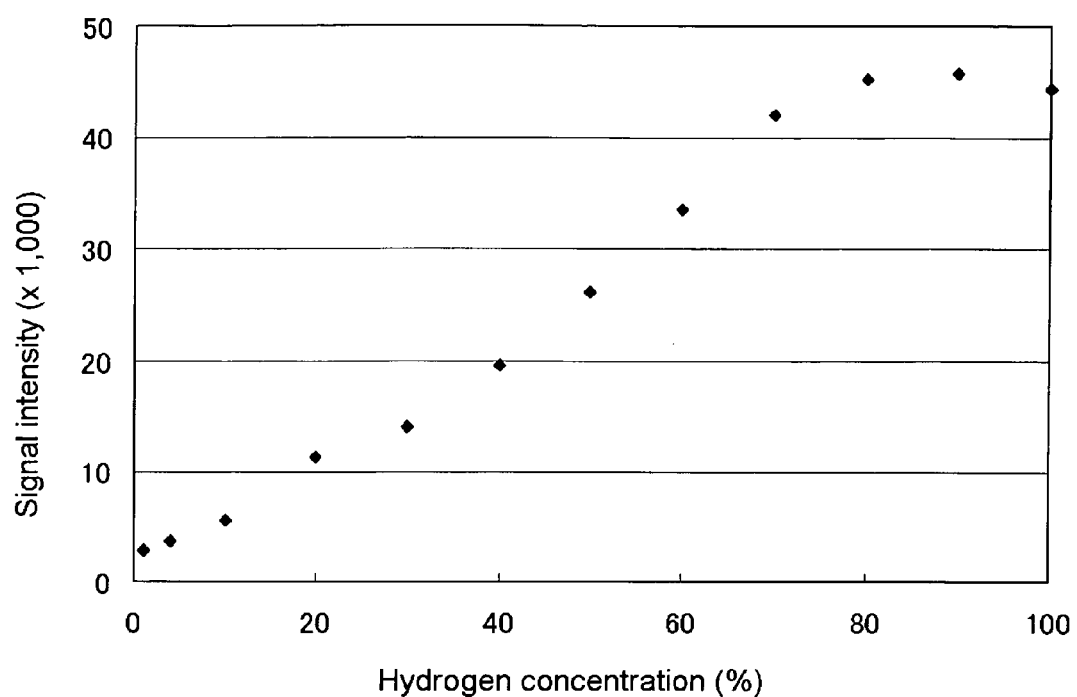
FIG. 15 is a graph showing the relationship between the hydrogen concentration and the intensity of the Raman scattering light according to Embodiment 2.

In addition, as a result of conducting an experiment by employing the system configuration shown in FIG. 13, hydrogen gas as the target gas, and a 266-nm fourth harmonic of a YAG laser as the laser beam source, correlation between the concentration of hydrogen gas and the spatial intensity of the Raman scattering light was confirmed as shown in FIG. 15. Therefore, the concentration of leaked hydrogen gas can be measured by detecting the spatial intensity of the Raman scattering light.

Embodiment 3

Figure 16:
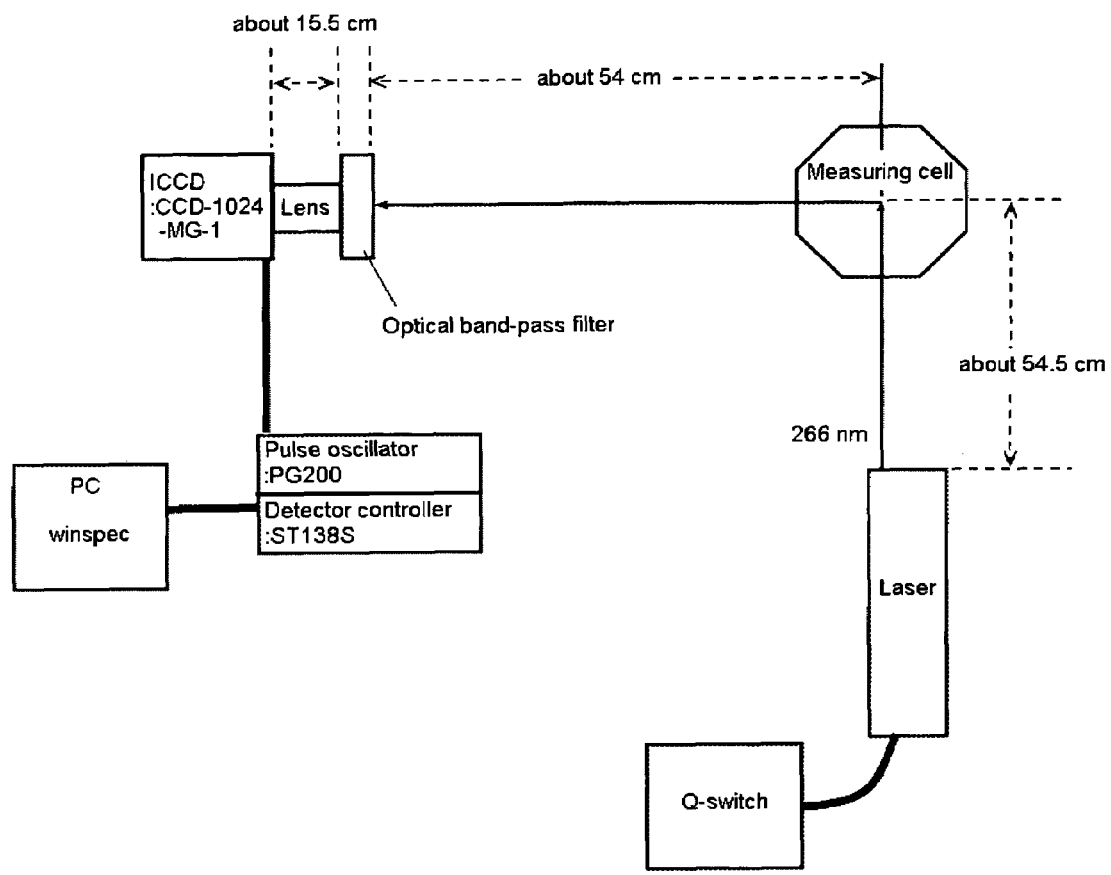
FIG. 16 is a schematic diagram showing the configuration of an experimental system for verifying visualization of leakage gas according to Embodiment 3.

FIG. 16 is a schematic diagram showing the configuration of an experimental system for verifying visualization of leakage gas.

Figure 17:
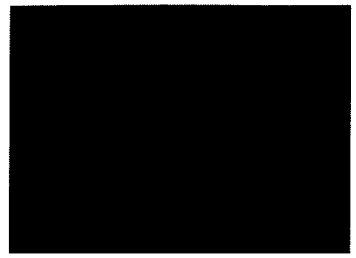
FIG. 17 shows the relationship between the hydrogen concentration and colored images according to Embodiment 3.
Figure 17:
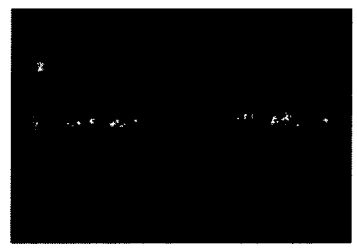
Figure 17:
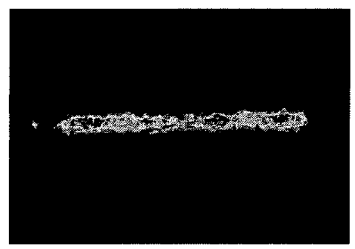
Figure 17:
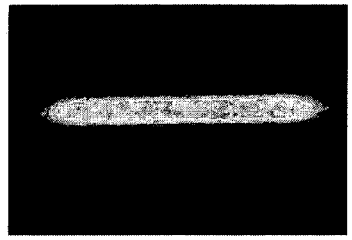
Figure 17:
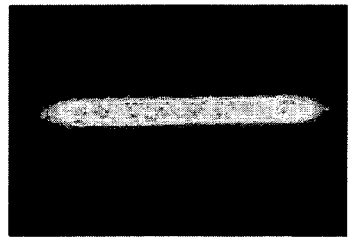
Figure 17:
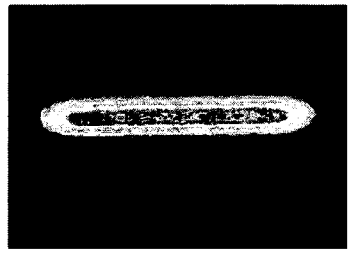

As a result of conducting an experiment for verifying visualization of leakage gas by employing the system configuration shown in FIG. 16, hydrogen gas as the target gas, and a 266-nm fourth harmonic of a YAG laser as the laser beam source, an image of the Raman scattering light was obtained as shown in FIG. 17.

The optical band-pass filter has a central wavelength of 299.1 nm, and its transmission wavelength range has a half width at half maximum of 1 nm.

FIG. 17 shows the colored images at various values of the hydrogen concentration. As shown in FIG. 17, the colored image becomes clearer by degrees as the hydrogen concentration increases.

Figure 18:
FIG. 18 shows a visualized image of a flame according to Embodiment 3.

FIG. 18 shows a visualized image of a hydrogen flame, which is obtained by coloring the image measured using the above-described system.

The optical band-pass filter has a central wavelength of 308.8 nm, and its transmission wavelength range has a half width at half maximum of 1.5 nm. While an exposure gate time was set to 80 μs for picking up an image in the measurement of this embodiment, a gate can be kept open.

Embodiment 4

Figure 19:
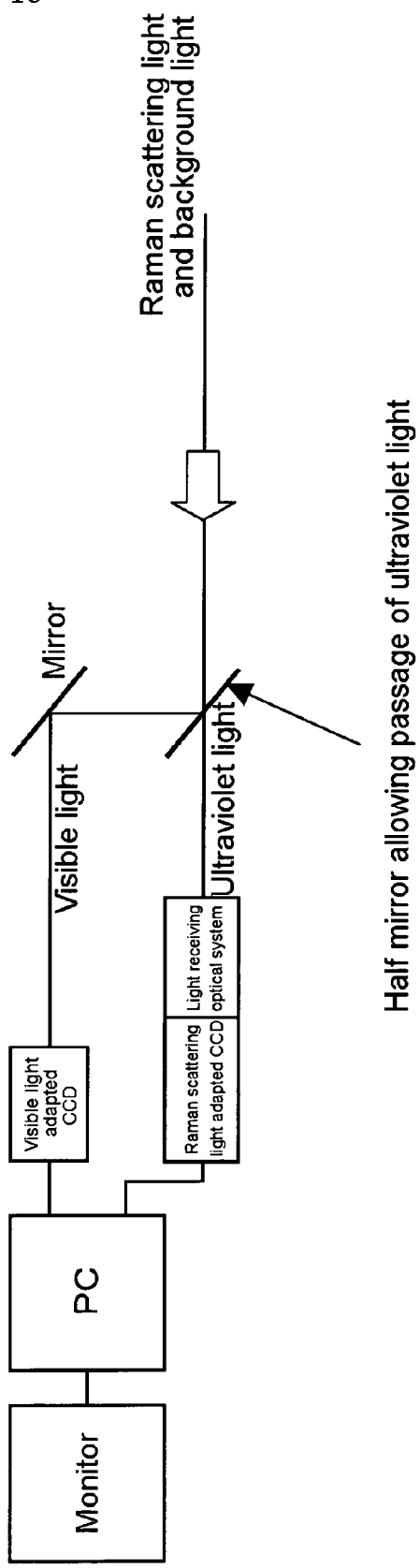
FIG. 19 is a block diagram of a gas leakage monitoring system according to Embodiment 4.

FIG. 19 shows another embodiment of the gas leakage monitoring system according to the present invention.

In the embodiment of FIG. 19, a half mirror allowing an ultraviolet light to pass through the mirror is used to introduce the Raman scattering light from the target gas to the Raman scattering light adapted camera for picking up an image of the leakage gas, while the background image is introduced to the visible light adapted camera so that optical axes of both the cameras are aligned with each other.

Embodiment 5

Figure 20:
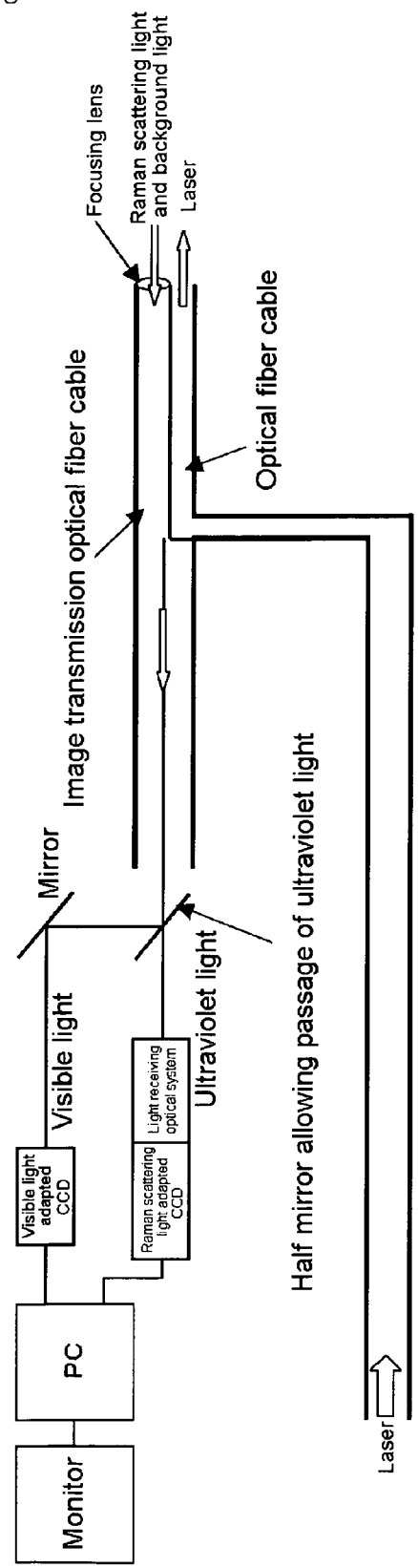
FIG. 20 is a block diagram of a gas leakage monitoring system according to Embodiment 5.

FIG. 20 shows still another embodiment of the gas leakage monitoring system according to the present invention.

In the embodiment of FIG. 20, the laser beam and the Raman scattering light are introduced through respective optical fiber cables. Therefore, this embodiment is suitable for detecting leakage gas in, e.g., a dead space of a structure or a closed conduit. The laser beam is irradiated through one optical fiber, and the Raman scattering light and the background light are focused at an end face of another optical fiber through a focusing lens. Then, a half mirror allowing an ultraviolet light to pass through the mirror is used to introduce the Raman scattering light from the target gas to the Raman scattering light adapted camera for picking up an image of the leakage gas, while the background image is introduced to the visible light adapted camera so that optical axes of both the cameras are aligned with each other.

Embodiment 6

Figure 21:
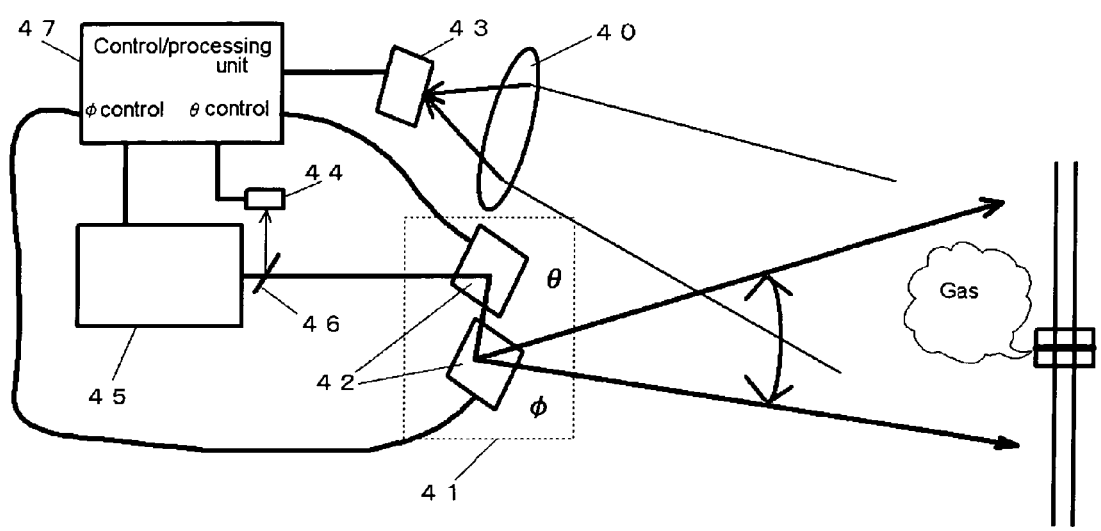
FIG. 21 is a block diagram of a laser-scanned leakage gas visualizing system according to Embodiment 6.

FIG. 21 shows the configuration of an embodiment of a laser-scanned gas leakage monitoring system according to the present invention.

The laser-scanned gas leakage monitoring system according to this embodiment comprises a laser transmission system made up of a laser unit 45, a beam distributor 46, a photo-detector 44 and a laser beam scanner 41 comprising two oscillating mirror 42, a light receiving system made up of a condenser lens 40 and a photo-detector 43, and control/-processing unit 47 including a control mechanism for the scanner 41 to control the irradiation position of the laser beam, also including a time synchronizing mechanism for controlling the timing of receiving the Raman scattering light with respect to the laser irradiation, and two-dimensionally imaging the position of the laser irradiation and the distribution of the Raman scattering light.

A part of a pulsing laser beam emitted from the laser unit 45 is changed in its direction by the beam distributor 46 so as to enter the photo-detector 44. A quartz plate and a photodiode are used respectively as the beam distributor 46 and the photo-detector 44.

An optical band-pass filter (not shown) having a center wavelength matched with the Raman wavelength of the target gas is disposed in front of a light receiving device of the photo-detector 43, and the condenser lens 40 for increasing the amount of received light is further disposed in front of the photo-detector 43. The photo-detector 43 is constituted by a photomultiplier tube or an APD (Avalanche photodiode).

By arranging another set of the photo-detector 43 along with an optical band-pass filter having a center wavelength matched with the wavelength of the laser beam and the condenser lens 40, it is possible to capture situations of the surroundings other than the target gas under monitoring in a three-dimensional way, and to confirm a spread of leakage gas from combination with the distance information obtained based on a Raman signal.

The leakage gas is detected by irradiating the laser beam emitted from the laser unit 45 to be scanned in a θ-direction (corresponding to a vertical tilt angle: Y axis) and in a φ-direction (corresponding to a horizontal angle: X axis) by the laser scanner 41, and receiving the Raman scattering light from the leakage gas by the photo-detector 43.

Based on the irradiation position of the laser beam and the signal from the photo-detector 43, data regarding a position (Xn, Yn) of the target gas under monitoring and data regarding the intensity of the Raman signal are calculated to sequentially display changes in the intensity of the Raman signal at a position (xn, yn) on the display, which corresponds to the target area. Alternatively, by recording the data of the position data and the intensity of the Raman signal in match with scanning of the laser beam, an image may be formed after scanning the entirety of the target area.

The distance from the monitoring system to the target gas is calculated from the information measured by the photo-detector 44. More specifically, a part of the laser beam emitted from the laser unit 45 is taken out by the beam distributor 46 and detected by the photo-detector 44. A time until receiving the signal from the photo-detector 43 is measured with a signal from the photo-detector 44 being a reference (0 second). The measured time interval represents a time required for the laser beam to reach the target gas and for the Raman scattering light to return from the target gas to the monitoring system. As a result, the distance from the monitoring system to the target gas can be calculated from the measured time interval.

Embodiment 7

The Raman scattering light from the target gas is scattered in larger amount in a direction exactly opposed to the direction in which the laser beam is irradiated (namely, a large part of the Raman scattering light is backscattered). Therefore, when the Raman scattering light is measured in a direction perpendicular to the irradiation direction of the laser beam (i.e., in a lateral direction) as in Embodiment 3 (i.e., in the case of the system configuration shown in FIG. 16), it may sometimes happen that the Raman scattering light is too weak to measure. In this embodiment, to avoid such a trouble, the Raman scattering light is measured from the backside by a gas leakage monitoring system configured to receive the backscattered light, as shown in FIG. 22.

A holed mirror is used to measure the Raman scattering light that is generated in a direction (backward) coaxial with the laser beam when the laser beam is irradiated to the measuring cell. The irradiated laser beam passes through a hole in the holed mirror, while the Raman light backscattered from the measuring cell is reflected by a mirror portion of the holed mirror to enter the lens, followed by being collected onto a slit of a spectrometer. On that occasion, because the collected light includes a component corresponding to the laser beam reflected by a window plate of the measuring cell, an attenuation filter for the laser beam (266 nm) is used to attenuate the laser beam component (266 nm).

Figure 22:
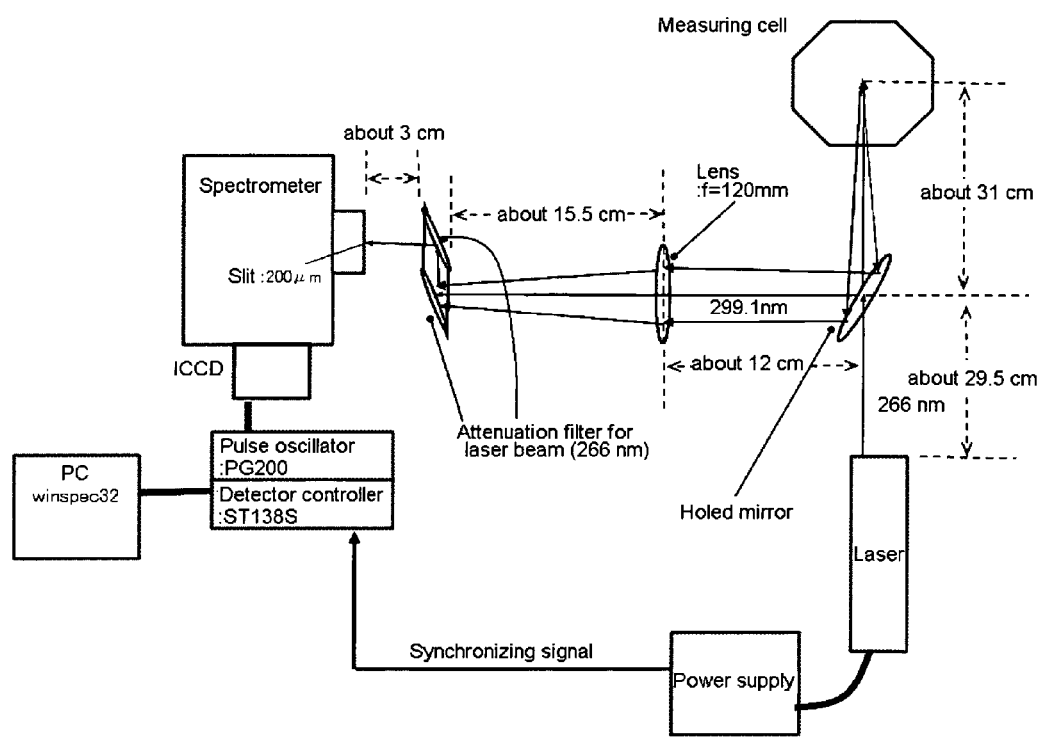
FIG. 22 is a block diagram of a gas leakage monitoring system for measuring a backscattered light according to Embodiment 7.
Figure 23A:
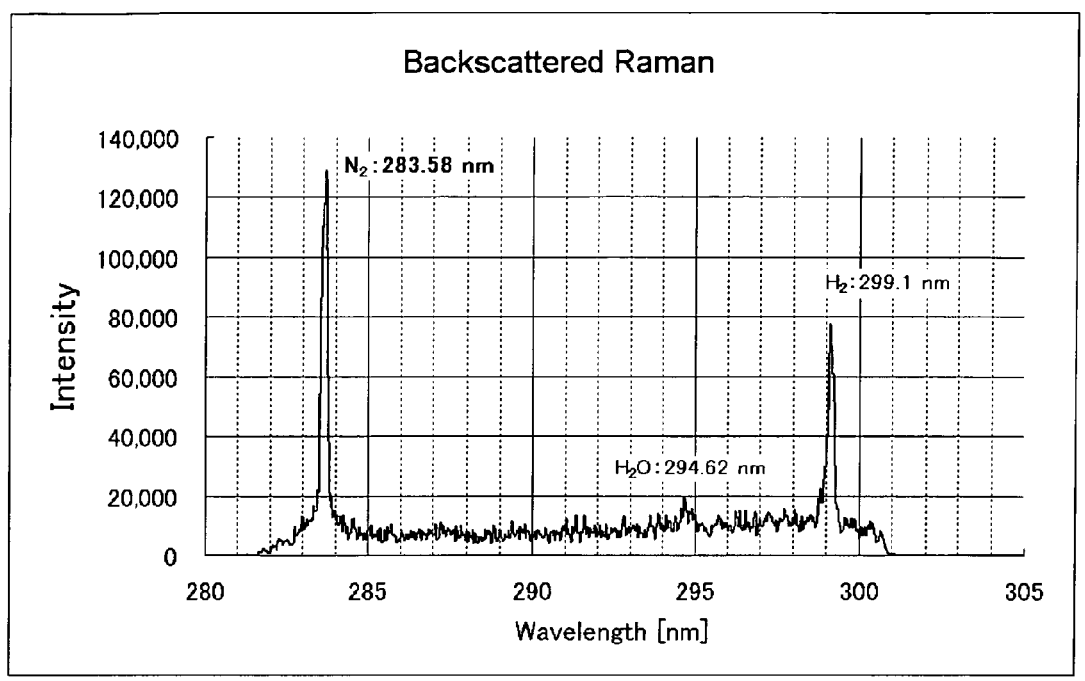
FIG. 23a is a graph showing the intensity of the Raman scattering light measured from the backside according to Embodiment 7.
Figure 23B:
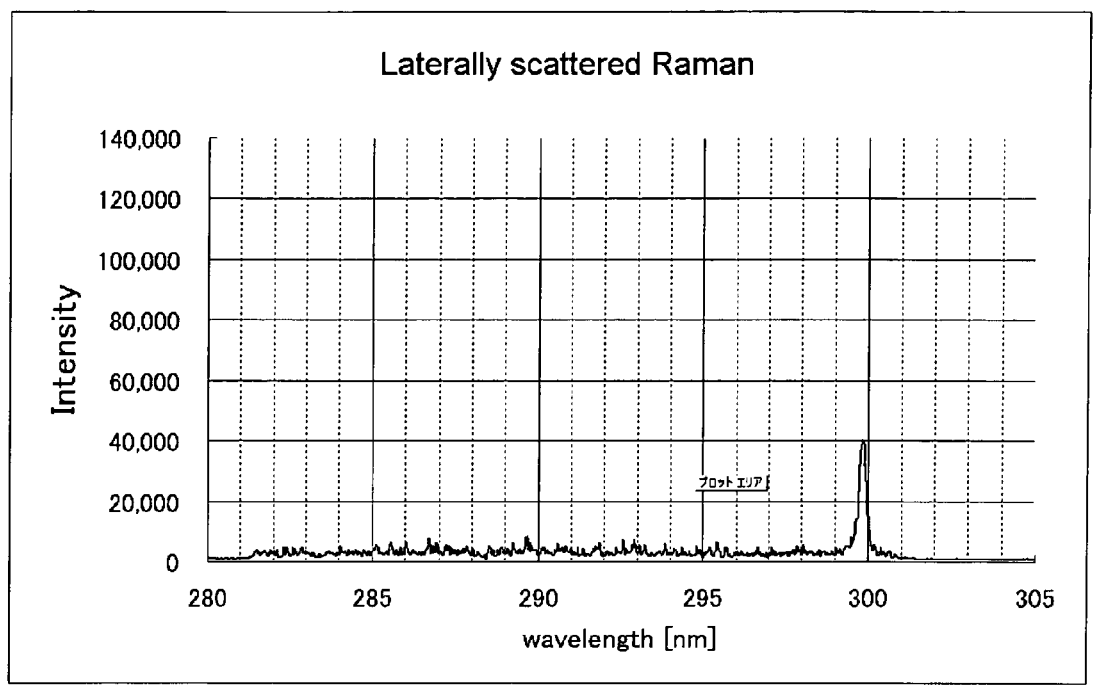
FIG. 23b is a graph showing the intensity of the Raman scattering light measured in a lateral direction according to Embodiment 7.

As a result of irradiating nitrogen gas ($N_2$), water vapor ($H_2O$), and hydrogen gas ($H_2$) with the system configuration shown in FIG. 22, a spectrum of the Raman scattering light was obtained as shown in FIG. 23a. On the other hand, as a result of measuring a spectrum of the Raman scattering light with the system configuration of FIG. 16 according to Embodiment 3, the spectrum was obtained as shown in FIG. 23b. As understood from those results, the system configuration for measuring the Raman scattering light from the backside is able to capture the Raman scattering light at larger intensity, and therefore it is more preferable as the configuration of the leakage gas detecting system.

INDUSTRIAL APPLICABILITY

According to the gas leakage monitoring method and system of the present invention, since an ultraviolet image of the Raman scattering light generated from target gas is selected by the optical band-pass filter of the image pickup means and the ultraviolet image is picked up through the image intensifier, it is possible to recognize the target gas even when it is colorless, transparent and invisible to the naked eye.

Also, the image of the target gas captured by the image pickup means can be converted into a visible image by the image processing means and displayed on the monitor, for example.

Further, the Raman scattering light generated from only the target gas can be selected by using the optical band-pass filter having a narrow band.

Moreover, by receiving the Raman scattering light generated from the target gas corresponding to the irradiated laser beam, a leakage of the target gas can be detected with certainty. Depending on the wavelength of the irradiated laser beam, a gas image can also be captured as an image of the scattered visible light.

In addition, since situations around a leakage point of the target gas can also be displayed as a background image on the monitor screen, it is possible to confirm the leakage point of the target gas in a short time and to promptly take actions such as stopping supply of the target gas.

According to the gas leakage monitoring method and system of the present invention, since an ultraviolet image of a flame is selected by the optical band-pass filter of the image pickup means and the ultraviolet image is picked up through the image intensifier, it is possible to recognize the flame even when it is invisible to the naked eye.

Also, the image of the flame captured by the image pickup means can be converted into a visible image by the image processing means and displayed on the monitor, for example.

Further, since situations around a position where a flame occurs, gas can also be displayed as a background image on the monitor screen, the flame generation position can be confirmed in a short time.

Moreover, by capturing an infrared image with the infrared image pickup means, a high-temperature dangerous region can be recognized in an area where there is another heat source, such as hot air or a leakage of current.

In addition, by displaying the flame image, the background image, and the infrared image in superimposed relation, it is possible to confirm the flame generation position and the high-temperature dangerous region, and therefore to smoothly take further actions for distinguishing a fire.

The invention claimed is:

1. A gas leakage monitoring method, comprising steps of:
    collecting a light at a wavelength in a target space to be monitored, thereby obtaining a collected light;
    converting the collected light into an electronic image;
    amplifying and converting the electronic image into an optical image and imaging a spatial intensity distribution of the light at the particular wavelength light; and
    superimposing the obtained image on a background image of the target space to be monitored and displaying leakage gas on the background image of the target space to be monitored.

2. The gas leakage monitoring method according to claim 1, further comprising a step of
    irradiating a laser beam to a target space to be monitored before the step of collecting a light,
    wherein the step of collecting a light includes collecting a Raman scattering light at a wavelength that is Raman-shifted by a predetermined value from the wavelength of the irradiated laser beam depending on a kind of target gas to be monitored, and wherein said spatial intensity distribution of the light is a spatial intensity distribution of the Raman scattering light.

3. The gas leakage monitoring method according to claim 2, wherein the Raman scattering light of the particular wavelength is collected only for a certain time calculated based on a return time of the laser beam or the Raman scattering light.

4. The gas leakage monitoring method according to claim 3, wherein the leakage gas is displayed in different colors depending on concentrations of the leakage gas in the target space to be monitored.

5. The gas leakage monitoring method according to claim 3, wherein the target gas to be monitored is selected from gases listed in Table 1 given below, and said predetermined values of the Raman shift are numerical values listed in Table 1

TABLE 1

| | Raman shift (cm$^{-1}$) |
|---|---|
| $CO_2$ | 1286 or 1388 |
| $O_2$ | 1556 |
| CO | 2145 |
| $N_2$ | 2331 |
| $H_2S$ | 2611 |
| $CH_4$ | 2914 or 3020 |
| $NH_3$ | 3334 |
| $H_2O$ | 3652 |
| $H_2$ | 4160. |

6. The gas leakage monitoring method according to claim 1,
wherein the step of collecting a light includes collecting, in a target space to be monitored, an ultraviolet light at a wavelength of about 309 nm which corresponds to an emission spectrum line of an OH-group,
wherein the spatial intensity distribution of the light is a spatial intensity distribution of the ultraviolet light at the particular wavelength, and
wherein the step of superimposing includes displaying a flame caused by hydrogen gas on the background image of the target space to be monitored.

7. The gas leakage monitoring method according to claim 6, the method further comprising the steps of collecting, in the target space to be monitored, an infrared spectrum of 7 μm to 14 μm, superimposing an infrared light image at the particular wavelength obtained through the imaging process and the ultraviolet light image at the particular wavelength obtained through the imaging process with each other, to thereby extract a common portion between the infrared and ultraviolet light images, and superimposing the extracted image on the background image of the target space to be monitored, thereby displaying a flame caused by hydrogen gas on the background image of the target space to be monitored.

8. The gas leakage monitoring method according to claim 7, the method further comprising the step of superimposing the infrared light image at the particular wavelength obtained through the imaging process and the background image of the target space to be monitored with each other, thereby displaying a high-temperature dangerous region on the background image of the target space to be monitored.

9. A gas leakage monitoring system comprising:
a light receiver including a condenser lens, an optical band-pass filter having a transmission wavelength center at a wavelength of a light spectrum from leakage gas, an image intensifier, an image pickup device, and a signal processing unit, wherein said light receiver collecting a light at a particular wavelength depending on a kind of gas to be monitored in a target space, converting the collected light into an electronic image, amplifying the electronic image and converting the amplified electronic image into an optical image and obtaining imaged spatial intensity distribution of the light at the particular wavelength;
a visual image pickup for capturing an image of visible light in the target space to be monitored;
an image processor for imaging a spatial intensity distribution of the light at the particular wavelength based on a signal from said light receiver, said image processor superimposing the image of visible light obtained by said visual image pickup and the imaged spatial intensity distribution of the light at the particular wavelength with each other and displaying leakage gas on the visible light image of the target space to be monitored.

10. The gas leakage monitoring system according to claim 9 further comprising:
a laser beam irradiator to irradiate laser beam to a target space to be monitored,
wherein said optical band-pass filter has a transmission wavelength center at the wavelength of a Raman scattering light spectrum from leakage gas,
wherein said light receiver collects a light at a wavelength that is Raman-shifted by a predetermined value from the wavelength of the irradiated laser beam depending on the kinds of target gas to be monitored, converts the collected light into an electronic image, amplifies the electronic image, and converts the amplified electronic image into an optical image again and obtains imaged spatial intensity distribution of the Raman scattering light at the particular wavelength, and
wherein said image processor images a spatial intensity distribution of the Raman scattering light at the particular wavelength based on a signal from said light receiver, superimposes the image of visible light obtained by said visual image pickup device and the imaged spatial intensity distribution of the Raman scattering light at the particular wavelength with each other, and displays leakage gas on the visible light image of the target space to be monitored.

11. The gas leakage monitoring system according to claim 10, further comprising synchronizing signal transmission means for transmitting a synchronizing signal for operating said light receiving means to collect the light only for a certain time calculated based on a return time of the laser beam or the Raman scattering light.

12. The gas leakage monitoring system according to claim 11, wherein said light receiver and said laser beam irradiation means are disposed in coaxial relation.

13. The gas leakage monitoring system according to claim 11, wherein said image processor displays the leakage gas in different colors depending on concentrations of the leakage gas in the target space to be monitored.

14. The gas leakage monitoring system according to claim 10, wherein the gas to be monitored is selected from gases listed in Table 2 given below, and said predetermined values of the Raman shift are numerical values listed in Table 2

TABLE 2

| | Raman shift (cm$^{-1}$) |
|---|---|
| $CO_2$ | 1286 or 1388 |
| $O_2$ | 1556 |
| CO | 2145 |
| $N_2$ | 2331 |
| $H_2S$ | 2611 |
| $CH_4$ | 2914 or 3020 |

TABLE 2-continued

| | Raman shift (cm$^{-1}$) |
|---|---|
| $NH_3$ | 3334 |
| $H_2O$ | 3652 |
| $H_2$ | 4160. |

15. The gas leakage monitoring system according to claim 10, wherein said light receiver further includes an optical band-pass filter having a transmission wavelength center at about 309 nm which corresponds to an emission spectrum line of an OH-group, and changes over said optical band-pass filter having the transmission wavelength center at the wavelength of the Raman scattering light spectrum from leakage gas and said optical band-pass filter having a transmission wavelength center at about 309 nm such that an ultraviolet light at a particular wavelength caused by a flame of hydrogen gas can be collected, and
  said image processor produces an image of a spatial intensity distribution of the ultraviolet light at the particular wavelength based on a signal from said light receiver, and superimposing the obtained image on the visible light image of the target space to be monitored, thereby displaying the flame caused by hydrogen gas on the visible light image of the target space to be monitored.

16. The gas leakage monitoring system according to claim 9,
  wherein the light receiver is an ultraviolet light receiver and the optical band-pass filter has a transmission wavelength center of about 309 nm which corresponds to an emission spectrum line of an OH-group, wherein said ultraviolet light receiver collects an ultraviolet light at a particular wavelength which is caused by a flame of leakage gas in the target space to be monitored, converts the collected ultraviolet light into an electronic image, amplifies the electronic image, and converts the amplified electronic image into an optical image again and obtains imaged spatial intensity distribution of the ultraviolet light at the particular wavelength,
  wherein said image processor images the spatial intensity distribution of the ultraviolet light at the particular wavelength based on a signal from said ultraviolet light receiver, and
  wherein the image processor superimposes the visible light image obtained by said visual image pickup device and the imaged spatial intensity distribution of the ultraviolet light at the particular wavelength with each other and displays a flame caused by hydrogen gas on the visible light image of the target space to be monitored.

17. The gas leakage monitoring system according to claim 16, further comprising infrared light receiver for capturing an image of an infrared spectrum of 7 μm to 14 μm in the target space to be monitored,
  said image processing means superimposing the infrared light image obtained by said infrared image pickup means and the imaged spatial intensity distribution of the ultraviolet light at the particular wavelength with each other, to thereby extract a common portion between the infrared and ultraviolet light images, and superimposing the extracted image on the visible light image obtained by said visual image pickup device, thereby displaying a flame caused by hydrogen gas on the visible light image of the target space to be monitored.

18. The gas leakage monitoring system according to claim 17, wherein said image processor superimposes the infrared light image obtained by said infrared light receiver and the visible light image obtained by said visual image pickup device with each other, thereby displaying a high-temperature dangerous region on the visible light image of the target space to be monitored.

* * * * *